US007285409B1

(12) United States Patent
Arruda et al.

(10) Patent No.: US 7,285,409 B1
(45) Date of Patent: Oct. 23, 2007

(54) ISOLATED GUM OPERON FROM *XYLLELA FASTIDIOSA*, ISOLATED NUCLEIC ACID MOLECULES THEREFROM, AND USES THEREOF

(75) Inventors: Paulo Arruda, Campinas (BR); Felipe Rodrigues da Silva, Campinas (BR); Edson Luis Kemper, Campinas (BR); Andre Vettorc, Campinas (BR); Adilson Leite, Campinas (BR); Marcio Jose da Silva, Campinas (BR)

(73) Assignee: Fundacao de Amparo a Pesquisa do Estado de Sao Paulo, Sao Paulo (BR)

( * ) Notice: Subject to any disclaimer, the term of this patent is extended or adjusted under 35 U.S.C. 154(b) by 0 days.

(21) Appl. No.: 09/567,465

(22) Filed: May 9, 2000

(51) Int. Cl.

| | |
|---|---|
| ***C12N 1/20*** | (2006.01) |
| ***C12N 5/02*** | (2006.01) |
| ***C12N 5/10*** | (2006.01) |
| ***C12N 1/00*** | (2006.01) |
| ***C12N 15/00*** | (2006.01) |
| ***C07H 21/00*** | (2006.01) |

(52) U.S. Cl. .................. 435/252.3; 435/325; 435/419; 435/254.11; 435/320.1; 536/23.1; 536/23.7

(58) Field of Classification Search .............. 536/23.1, 536/23.2, 23.7; 435/320.1, 325, 419, 252.3, 435/254.11; 530/350
See application file for complete search history.

(56) References Cited

FOREIGN PATENT DOCUMENTS

WO 87/05938 * 10/1987

OTHER PUBLICATIONS da Silva et al. (2001) FEMS Microbiol Lett 203: 165-171.*
Branden et al. "Introduction to Protein Structure", Garland Publishing Inc., New York, 1991, p. 247.*
Witkowski et al. (1999) Biochemistry 38:11643-11650.*
Lambais et al. (2000) Curr Opin Microbiol 3:459-462.*
Vojnov, et al, "Evidence for a role for the gumB and gumC gene products in the formation of xanthan from its pentasaccharide repeating unit by *Xanthomonas campestris*," Microbiology 144:1487-1493 (1998).
Becker, et al, "Xanthan gum biosynthesis and application: a biochemical/genetic perspective," Appl. Microbiol Biotechnol 50: 145-152 (1998).
Thompson, et al, "The CLUSTAL_X windows interface: flexible strategies for multiple sequence alignment aided by quality analysis tools" Nucl. Acids Res 25(24): 4876-4882 (1999).
Chou, et al, "The *Xanthomonas campestris* gumD Gene Required for Synthesis of Xanthan Gum Is Involved In Normal Pigmentation and Virulence In Causing Black Rot," Biochem & Biophys: Res. Comm. 233: 265-269 (1997).
Levy, et al, Dynamic Simulations of The Molecular Conformations of Wild Type and Mutant Xanthan Polymers Suggest that Conformational Differences May Contribute To Observed Differences in Viscosity. Biopolymers 38:251-272 (1996).
Talukdar, et al, "Rheological Characterization of Xanthan Gum and Hydroxypropylmethyl Cellulose with Respect to Controlled-Release Drug Delivery," J. Pharm. Sci. 85(5): 537-540 (1996).
Kondo, et al, "Combination Effects of α-Cyclodextrin and Xanthan Gum on Rectal Absorption and Metabolism of Morphine from Hollow-Type Suppositories in Rabbits." Biol. Pharm. Bull. 19(2): 280-286 (1996).
Watanabe, et al, "Investigation on Rectal Absorption of Indomethacin from Sustained-Release Hydrogel Suppositories Prepared with Water-Soluble Dietary Fibers, Xanthan Gum and Locust Bean Gum," Biol. Pharm. Bull. 16(4): 391-394 (1993).
Harding, et al, "Identification, genetic and biochemical analysis of genes involved in synthesis of sugar nucleotide precursors of xanthan gum," J. Gen. Microbiol 139: 447-457 (1993).
Watanabe, et al, "Factors Affecting Prednisolone Release from Hydrogels Prepared with Water-Soluble Dietary Fibers, Xanthan and Locust Bean Gums," Chem. Pharm. Bull. 40(2): 459-462 (1992).
Köplin, et al, "Genetics of Xanthan Production in *Xanthomonas campestris*: the xanA and xanB Genes are Involved in UDP-glucose and GDL-mannose Biosynthesis," J. Bacteriol. 174(1): 191-199 (1992).
Hassler, et al, "Genetic Engineering of Polysaccharide Structure: Production of Variants of Xanthan Gum in *Xanthomonas campestris*," Biotechnol. Proj. 6:182-187 (1990).
Harding, et al, "Genetic and Physical Analyses of a Cluster of Genes Essential for Xanthan Gum Biosynthesis in *Xanthomonas campestris*," J. Bacteriol. 169(6): 2854-2861 (1987).
Osilesi, et al, "Use of xanthan gum in dietary management of diabetes mellitus," Am. J. Clin. Nutr. 42(4): 597-603 (Oct. 1985).

* cited by examiner

*Primary Examiner*—David J. Steadman
(74) *Attorney, Agent, or Firm*—Fulbright & Jaworski LLP

(57) ABSTRACT

This invention relates to the isolation and characterization of an operon from the organism *Xylella fastidiosa*. This operon, referred to as the XfGUM operon, contains 9 genes, and is involved in the production of a compound with xanthan gum like properties. The expression products of the operon and genes are also a part of the invention, as are various uses of these.

10 Claims, 3 Drawing Sheets

Xanthomonas campestris GUM Operon Sequences

Fig 1A (GumB) (SEQ ID NO: 20)

MSLGACSTGPEMASSLPHPDPLAMSTVQPEYRLAPGDLLLVKVFQIDDLERQVRIDQNGHISLPLIGDVK
AAGLGVGELEKLVADRYRAGYLQQPQISVFVQESNGRRVTVTGAVDEPGIYPVIGANLTLQQAIAQAKGV
STVASRGNVIVFRMVNGQKMIARFDLTEIEKGANPDPEIYGGDIVVVYRSDARVWLRTMLELTPLVMVWR
AYR

Fig 1B (GumC) (SEQ ID NO: 21)

MDYWRALVSQLWLIILIAVGALLLAFGITMLMPEKYRATSTLQIERDSLNVVNVDNLMPVESPQDRDFYQ
TQYQLLQSRSLARAVIREAKLDQEPAFKEQVEEALAKAAEKNPEAGKSLDSRQAIVERSLTDTLLAGLVV
EPILNSRLVYVNYDSPDPVLAAKIANTYPKVFIVSTQERRMKASSFATQFLAERLKQLREKVEDSEKDLV
SYSTEEQIVSVGDDKPSLPAQNLTDLNALLASAQDARIKAESAWRQASSGDGMSLPQVLSSPLIQSLRSE
QVRLTSEYQQKLSTFKPDYPEMQRLKAQIEESRRQINGEVINIRQSLKATYDASVHQEQLLNDRIAGLRS
NELDLQSRSIRYNMLKRDVDTNRQLYDALLQRYKEIGVASNVGANNVTIVDTADVPTSKTSPKLKLNLAL
GLIFGVFLGVAVALVRYFLRGPSPRSRLN

Fig 1C (GumD) (SEQ ID NO: 22)

MLLADLSSATYTTSSPRLLSKYSAAADLVLRVFDLTMVVASGLIAYRIVFGTWVPAAPYRVAIATTLLYS
VICFALFPLYRSWRGRGLLSELVVLGGAFGGVFALFAVHALIVQVGEQVSRGWVGLWFVGGLVSLVAART
LLRGFLNHLRTQGVDVQRVVVVGLRHPVMKISHYLSRNPWVGMNMVGYFRTPYDLAVAEQRQGLPCLGDP
DELIEYLKNNQVEQVWISLPLGERDHIKQLLQRLDRYPINVKLVPDLFDFGLLNQSAEQIGSVPVINLRQ
GGVDRDNYFVVAKALQDKILAVIALMGLWPLMLAIAVGVKMSSPGPVFFRQRRHGLGGREFYMFKFRSMR
VHDDHGTTIQQATKNDTRITRFGSFLRRSSLDELPQIFNVLGGSMSIVGPRPHAAQHNTHYEKLINHYMQ
RHYVKPGITGWAQVNGFRGETPELRTMKKRIQYDLDYIRRWSLWLDIRIIVLTAVRVLGQKTAY

Fig 1D (GumE) (SEQ ID NO: 23)

MLIQMSEQARVRWHNALIELTLLTGVGYNLLLALINANVFTVRPVITYAVEFLVYAACFLLGLGSMSRQR
IAMIFGGLGLIVTLMFVRFLVNWQIDPKFFRDALVVFAFVVLGSAYTGSLPKLFIRMTIIVSLVAAFELA
MPSAYGDLVNPKSFFVNARGMSAEGFWNEDSNLFVSATRPGERNFLPGSNLPRASSWFIEPVTMGNYICF
FTAIVLTFWRWMRPSMLILSIGLIGFMIVASDGRLAAGTCVLMVLLSPLLKRMDQRLAFLLFLFVIASAW
LLVWMTGITAYQDTTMGRIFFTVNSMNNLSFESWMGLDFAQAYRYFDSGISYFIASQSIVGVLAFLLSYS
FLLLMPSKEGQLFKNQAMFAFALSLLVSNGYFSIKTSALWWFVCGCMWHLMPAASAVPVRDESKEDPTDN
GVHVPLPAGAPR

Fig 1E (GumF) (SEQ ID NO: 24)

MNTVTGASGTSAPVQAAGARAFASGRSRDPRIDATKAIAILLVVFCHAKGVPHGMTLFAYSFHVPLFFLV
SGWLAAGYASRTTSLLQTITKQARGLLLPYVVFYLLGYVYWLLTRNIGEKAARWGSHPWWEPIVSMFTGV
GPDLYVQPPLWFLPVMLVTVIGYVLLRRWMPPLVIAAVAVVLAWFWMNWFPLQHMRLFWGLDVLPVSLCF
YALGALLIHVSPYLPTSLPGSALVTVVLAALVAWLAGVNGRIDVNMLEFGRQHAVFLLSAVAGSLMVICA
ARMVQEWTWLQWIGRNTLLILCTHMLVFFVLSGVAALAGGFGGARPGLGWAIFVTLFALVASVPLRWFLM
RFAPWTLGARPVSA

Fig 1F (GumH) (SEQ ID NO: 25)

MKVVHVVRQFHPSIGGMEEVVLNVARQHQANSADTVEIVTLDRVFTDPSAQLAQHELHQGLSITRIGYRG
SSRYPIAPSVLGAIRSADVVHLHGIDFFYDYLALTKPLHGKPMVVSTHGGFFHTAYASRMKQIWFQTLTR
TSALAYARVIATSENDGDLFAKVVAPSRLRVIENGVDVEKYAGQGARAPGRTMLYFGRWSVNKGLIETLE
LLQAALTRDPQWRLIIAGREYDLNEADLRKAIAERGLQDKVQLSMSPSQQQLCALMQQAQFFVCLSRHEG
FGIAAVEAMSAGLIPILSDIPPFVRLATESGQGVIVNRDRIQAAADSVQALALQANADFDARRTATMAYV
ARYDWRHVVGRYIDEYHAALGTPRTQEAVR

Fig 1G (GumJ) (SEQ ID NO: 26)

MTAETSTMTSPTPPPRSLGSRAAGAAVTMIGQSAKMIVQFGGIVLLARLLTPYDYGLMAMVTAIVGAAEI
LRDFGLSAAAVQAKHVSREQRDNLFWINSGIGLMLSVVVFASAHWIADFYHEPALVTISQALAVTFLLNG
MTTQYRAHLSRGLRFGQVALSDVGSQVLGLGAAVAAALAGWGYWALIVQQVVQAIVNLIIAGACARWLPR
GYARQAPMRDFMSFGWNLMAAQLLGYASRNVGQVIIGWRTGPDALGLYNRAFQLLMMPLNQINAPATSVA
LPVLSQLQDERERYSAFLLRGQTVMVHLIFALFAFACALAMPLIVLVLGEQWREAVPLFQVLTLGGIFQT
ASYATYWVFLSKGLMREQLVYSLVGRILLIACIFVGSRWGAMGVAIGYSFGLLLIWPLSLVWIGKITDAP
VGALFVNAMRALVAYGIAGGCAYYASVTVGGPLWQQLLVGAGAMALVCLLALAWPGFRRDVVAIVNIRKL
LTQAKARR

Fig 1H (GumK) (SEQ ID NO: 27)

MFRWYAAHPPKQLLDWMRESDVIVFESGIAVAFIELAKRVNPAAKLVYRASDGLSTINVASYIEREFDRV
APTLDVIALVSPAMAAEVASRDNVFHVGHGVDHNLDQLGDPSPYAEGIHAVAVGSMLFDPEFFVVASKAF
PQVTFHVIGSGMGRHPGYGDNVIVYGEMKHAQTIGYIKHARFGIAPYASEQVPVYLADSSMKLLQYDFFG
LPAVCPNAVVGPYKSRFGYTPGNADSVIAAITQALEAPRVRYRQCLNWSDTTDRVLDPRAYPETRLYPHP
PTAAPQLSSEAALSH

Fig 1I (GumM) (SEQ ID NO: 28)

MHGQPAGVETATVSAATPAQGVVIPLGGFPVLSTTQEAFALDLFHALAAHQPRRVFFANTNFIVQCQALR
ARMQAPAVRIVNDGIGMDLAARLIHGRRFAGNLNGTDLIPYLCREAAQPLKFFLLGGRPGVGKTAAATLT
GTLGQQVVGMCDGYGEFAAAGEGLAERINRSGADVLLVAFGNPLQERWILDHSEALQVPLVFGVGALLDF
LSGTAKRAPNWVRRLHMEWMYRLLNEPRRLLKRYSWDLLVFFRTCLRAGKQLA

ISOLATED GUM OPERON FROM *XYLLELA FASTIDIOSA*, ISOLATED NUCLEIC ACID MOLECULES THEREFROM, AND USES THEREOF

This invention was made with FAPESP support.

FIELD OF THE INVENTION

This invention relates to the isolation of an operon of the microorganism *Xylella fastidiosa*. More particularly, it relates to the isolation of such an operon which comprises nine genes, referred to as "xfgum B, C, D, E, F, H, J, K and M" hereafter. Also a part of the invention are isolated nucleic acid molecules for each of these 9 separate genes. Also a part of the invention are expression vectors which comprise the operon, or one or more of the component genes, in operable linkage with a promoter, recombinant cells which include the operon or one or more of the genes, the expression product of these genes, and various uses thereof.

BACKGROUND AND PRIOR ART

Xanthan gum is an exopolysaccharide ("EPS" hereafter) produced by the phytopathogenic bacterium *Xanthomonas campestris* (Ielpi et al., 1981, FEBS Lett. 130:253-256). The biosynthesis of this extracellular polysaccharide in X campestris is directed by a cluster of 12 genes, gumB-gumM (Becker et al., 1998, Appl Microbiol Biotechnol, 50:145-152; Vojnov et al., 1998, Microbiology 144; 487-493). It is composed of polymerized pentasaccharide repeating units which are assembled by the sequential addition of glucose-1-phosphate, glucose, mannose, glucuronic acid, and mannose on a polyprenol phosphate carrier (Ielpi et al., 1993, J. Bacteriol. 175:2490-2500). The pentasaccharide repeating unit is also O-acetylated and pyruvylated to various degrees (Ielpi et al., 1993, J. Bacteriol. 175:2490-2500).

Transformation with a gene cluster carrying gumB and gumC restored xanthan production in deficient mutants, suggesting that gumB and gumC are both involved in the translocation of xanthan across the bacterial membrane (Vojnov et al., 1998, Microbiology 144: 487-493).

Two gene groups are involved in xanthan biosynthesis: the genes xpsIII, xps IV and xps VI, which are responsible for synthesis of UDP-glucose, UDP-glucuronic acid and GDP-mannose, respectively (Harding et al., J. Bacteriol 169: 2854-2861 (1987); Harding et al., J. Gen Micobiol 139: 447-457 (1993); Hötte et al., 1999; Köplin et al. J. Bacteriol 174: 191-199 (1992), 1992) and the genes gum or xpsI, which encode the enzymes involved in the polymerization of the pentasaccharide linked to polyprenol phosphate and secretion of the EPS to the extracellular medium (Ielpi et al., 1992; supra Ielpi et al., 1993 supra).

The *X. campestris* gum genes are grouped in an operon (GUM operon) of about 16 Kb in length, containing 12 genes designated gumB, C, D, E, F, G, H, I, J, K, L and M. The gumD gene encodes the enzyme glucosyltranferase I, responsible for the transference of the glucose-1-phosphate of UDP-glucose to the polyprenol phosphate carrier to form the lipid-monosaccharide. GumM encodes the enzyme glucosyltranferase II, which catalyzes the addition of the second glucose residue to form the lipid-disaccharide. GumH encodes the enzyme glucosyltranferase III, which catalyzes the addition of the first mannose residue to form the lipid-trisaccharide. GumK encodes the enzyme glucosyltranferase IV, which catalyzes the addition of a glucuronic acid residue to form the lipid-tetrasaccharide. GumI encodes the enzyme glucosyltranferase V, which catalyzes the addition of a second mannose residue to form the lipid-pentasaccharide. GumF encodes the enzyme acetyltransferase I which catalyzes acetylation of the internal mannose residue. GumG encodes the enzyme acetyltransferase II which catalyzes the acetylation of the external mannose residue. Finally, gumL encodes the enzyme pyruvate ketal transferase which catalyzes pyruvylation of the external mannose residue. GumB, C and E are involved in the polymerization and secretion of the EPS through the bacterial membrane while gumJ is thought to be involved in a parallel stage of polymerization and secretion of the EPS (Ielpi et al., 1992 supra; Ielpi et al., 1993 supra).

Xanthan has wide commercial application as a viscosifier of aqueous solutions. It is used in both the food and non-food industries and also as a stabilizer of suspensions, emulsions, and foams. Mutant *Xanthomonas* strains defective in the xanthan biosynthesis pathway have been shown to synthesize and polymerize xanthans with variant structures, similar rheological properties, and different viscosities (Hassler and Doherty, 1990, Biotechnical Prog 6:182-187). Acetylation and pyruvylation can affect the viscometric properties of xanthan. The presence of pyruvate increases viscosity, whereas acetate decreases viscosity (Hassler and Doherty, supra). The elimination of sugar residues from xanthan side chains also affects viscosity. As compared to wild-type xanthan, polymers lacking the terminal mannose (polytetramers) are poor viscosifiers. In contrast, polymers lacking both the terminal mannose and glucuronic acid residues (polytrimers) are superior viscosifiers (Hassler and Doherty, supra). A nonacetylated and an acetylated tetramer, both lacking the side-chain terminal mannose residue and in the first case lacking an acetate group on an internal mannose residue showed higher viscosity (in the first case) and lower viscosity (in the second case) when compared to a wild-type bacteria (Levy et al., 1996, Biopolymers 38:251-272). A major conformational difference between the higher and lower viscosities is the increased amount of open helical backbone and the increase in the side-chain flexibility high viscosity (Levy et al., 1996, Biopolymers 38:251-272).

Xanthan has also been used as a drug stabilizer, to improve drug absorption, to delay drug release and can also be used in controlled-release formulations (Talukdar et al., 1996, J Pharm Sci 185:537-540). In combination with xanthan gum, alpha-cyclodextrin reduced the first-pass metabolism of morphine in the rectal mucosa and by the liver, and was shown to improve the apparent rectal bioavailability of the opioid about 4 fold (Kondo et al., 1996, Biol Pharm Bull 19:280-286). Xanthan-alginate has been used for encapsulation of enzymes. The xanthan-alginate spheres showed 75% of maximum urease activity even after 20 repeated uses under optimal conditions (Elgin, 1995, Biomaterials 16:1157-1161).

Sustained-release hydrogel suppositories prepared with water-soluble dietary fibers, xanthan gum and locust bean gum have been shown to sustain drug release for a much longer time than commercial suppositories. The mean residence time was higher, without a decrease in the area under the plasma concentration vs. time curve. Histopathological studies showed good biological safety of the hydrogel suppositories to the rectal mucosa. These results suggested that IMC hydrogel suppositories prepared with xanthan gum and locust bean gum were a practical rectal preparation having prolonged action and reduced side effects (Watanabe et al., 1993, Bio Pharm Bull 16:391-394).

The apparent release rate of prednisolone from hydrogels prepared with xanthan decreased with increasing gum concentration, suggestion that the diffusion of drug molecules was mainly controlled by the density of the three-dimensional network structure in the matrix. These results indicated that drug release could be controlled not only by the density of the network structure but also by the microscopic viscosity of the hydrogels (Watanabe et al., 1992, Chem Pharm Bull 40:459-462).

A neomycin-furazolidone-xanthan complex has been shown to increase the antimicrobial activity of the drug (Dumitriu et al., 1993, J. Biomater 7:256-276).

Xanthan gum has also been shown to alleviate diabetes mellitus. Administration of xanthan gum lowered fasting and postload serum glucose and reduced fasting levels of total plasma cholesterol in diabetic subjects. Xanthan gum also tended to lower fasting and postload levels of gastrin and gastric inhibitory polypeptide (GIP) and fasting levels of total and VLDL triglyceride and cholesterol in VLDL and LDL fractions. Subjects reported a sense of fullness after consuming xanthan muffins but no severe digestive symptoms (Osilesi et al., 1985, Am J Clin Nutr 42:597-603).

Several factors have been associated with pathogenicity of phytopathogenic bacteria, including production of extracellular enzymes, production of exopolysaccharides, production of toxins and phytohormones along with factors mediating specific plant pathogen interactions (Agrios, 1988, Plant Pathology, 3rd edition, Academic Press; Alippi, 1992, Agronomie 12:115-122). The role of EPSs in the pathogenicity of several bacteria is well known. They are associated with (i) cell death due to occlusion of xylem vessels, (ii) mucoid lesions and (iii) helping plant/pathogen interaction and bacterial growth in the plant tissues.

Several groups have investigated the role of xanthan in *Xanthomonas* pathogenicity. Although it was believed for a long time that xanthan gum is key to pathogenicity, many authors did not succeed in demonstrating a direct link between this EPS and pathogenicity (Kamoun and Kado, 1990, J. Bacteriol 172:5165-5172). Recently, it has been demonstrated that deletion of gumD (Chou et al., 1997, Biochem Biophys Res. Commun 233:265-269) or alterations in the later stages of xanthan biosynthesis (Katzen et al., 1998, J. Bacteriol 180:1607-1617) reduced virulence in causing black rot in broccoli and decreased the aggressiveness of *Xanthomonas* against plants. Although the symptoms of *X. fastidiosa* infection of orange trees are well known, e.g., leaf clorosis, nutritional deficiency symptoms, reduced fruit size, etc. (De Negri, 1990, Com. Tec. No. 82, Ext. Rural, Cats, Compinas; Malavolta et al., 1990, Cordeiropolis, v. 11, n. 1, p. 15-18), the mechanism by which the bacteria causes the disease is unknown. Bacterial infection depends on insect vectors such as *Oncometopia facialis, Acrogonia terminalis* and *Dilobopterus costalimai* (Gravena, et al., 1997, "Os vetores de *Xylella fastidiosa* In: Clorose Variegada do Citros"). These insects, when feeding on xylem nutrients, introduce the bacteria into the vessel where bacteria grows fastidiously (Lopes et al., 1996, "*Xylella fastidiosa*," Fitopathologin Brasileira, Brasilia v. 21, Suplemento p. 343; Roberto et al., 1996, Fitopatologia Brasileira, Brasilia v. 21, n. 4, p. 517-18). The EPS synthesized by the XfGUM operon, which is a feature of the invention, might be directly involved in the pathogenicity causing Citrus Variegated Clorosis in orange trees and other diseases in plants, such as coffee and grape plants.

SUMMARY OF THE INVENTION

The invention relates, in part, to a nucleic acid molecule of about 12710 nucleotides which encodes the members of the XfGUM operon, including genes for xfgumB, xfgumC, xfgumD, xfgumE, xfgumF, xfgumH, xfgumJ, xfgumK and xfgumM and the uses of such operons, as well as the proteins encoded thereby. These can be used, e.g., to control orange tree diseases, such as Citrus Variegated Clorosis (CVC) and diseases caused by the bacteria in other plants. The EPS produced by the enzymes encoded by the XfGUM operon may cause the diseases by occluding the xylem vessels, or by participating in the mechanism of bacteria infection, adhesion and spreading; however, applicants do not limit themselves to any single theory of operation. The invention also relates to the use of components of the XfGUM operon for production of exopolysaccharides, useful industrial and/or medical application of this new gum and structural gums variants, using *Xylella fastidiosa* or any other bacteria as a host.

The invention is based in a number of unanticipated and surprising discoveries. One is the discovery of a DNA sequence of 12710 nucleotides in the genome of the phytopathogenic bacteria *Xylella fastidiosa*. A xanthan GUM operon has been found previously only in *Xanthomonas campestris*. Another is the finding that the XfGUM operon lacks genes gumI, gumG and gumL, which encode the enzymes glucosyltransferase V, acetyltranferase II and pyruvate ketal transferase, respectively. The absence of these genes indicate that the XfGUM operon encodes the enzymes necessary to synthesize an exopolysaccharide composed of tetrameric units consisted of glucose, glucose, mannose and glucuronic acid and that, in view of the absence of the genes encoding the acetyltransferase II and pyruvate ketal transferase, the resulting tetrasaccharide is not pyruvylated at all and, as demonstrated for *Xanthomonas*, its mannose may be only partially acetylated. These findings indicate that XfGUM encodes the enzymes that produce a new gum with new Theological and chemical properties.

The invention includes, inter alia, (a) nucleotide sequences containing the structural and regulatory regions of the XfGUM operon that encode the enzymes glycosyltranferase I, glycosyltranferase II, glycosyltranferase III, glycosyltranferase IV, and acetyltransferase I, as well as the proteins referred to hereafter as GUMB, GUMC, GUME and GUMJ; (b) the expression of such nucleotide sequences in cells; (c) the isolated enzymes, proteins, and active forms thereof, as well as mutants, fragments, and fusion proteins; (d) the uses of the enzymes and/or proteins encoded by the GUM-like Operon in screening methods for identifying compounds that are useful in controlling diseases caused by *Xylella fastidiosa* and/or related organisms; (e) the engineering of bacterial hosts to express the enzymes and/or proteins encoded by XfGUM; and (f) the use of the engineered hosts expressing the enzymes and/or proteins encoded by XfGUM to produce the exopolysaccharide for industrial and/or medical applications, and for animal use, including humans.

BRIEF DESCRIPTION OF THE FIGURES

FIGS. 1A to 1I present *Xanthomonas campestris* Gum operon sequences of the Prior Art.

FIG. 1A presents the amino acid sequence of *Xanthomonas campestris* protein GumB (SEQ ID NO: 20).

FIG. 1B presents the amino acid sequence of *Xanthomonas campestris* protein GumC (SEQ ID NO: 21).

FIG. 1C presents the amino acid sequence of *Xanthomonas campestris* protein GumD (SEQ ID NO: 22).

FIG. 1D presents the amino acid sequence of *Xanthomonas campestris* protein GumE (SEQ ID NO: 23).

FIG. 1E presents the amino acid sequence of *Xanthomonas campestris* protein GumF (SEQ ID NO: 24).

FIG. 1F presents the amino acid sequence of *Xanthomonas campestris* protein GumH (SEQ ID NO: 25).

FIG. 1G presents the amino acid sequence of *Xanthomonas* campestris protein GumJ (SEQ ID NO: 26).

FIG. 1H presents the amino acid sequence of *Xanthomonas* campestris protein GumK (SEQ ID NO: 27).

FIG. 1*i* presents the amino acid sequence of *Xanthomonas* campestris protein GumM (SEQ ID NO: 28).

DETAILED DESCRIPTION OF THE PREFERRED EMBODIMENTS

Figure 2:
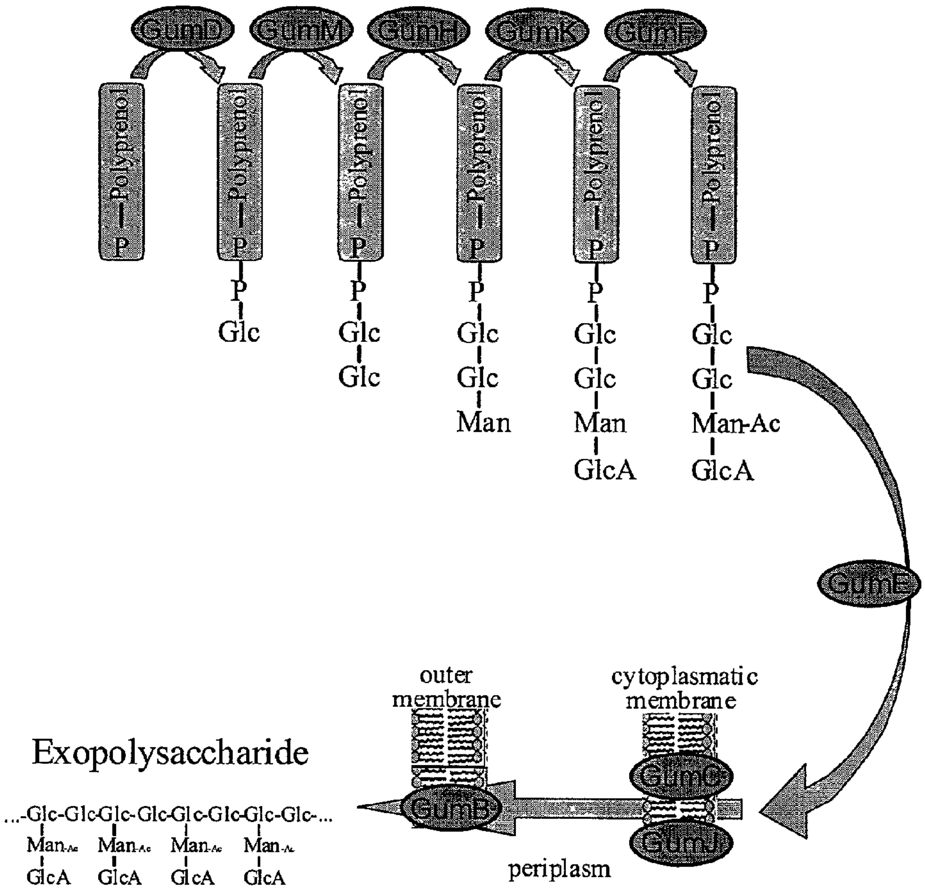
FIG. 2 sets forth a proposed biosynthetic pathway using the components of the invention.

The present invention relates to a nucleic acid molecule of about 12710 nucleotides of the *Xylella fastidiosa* genome that encodes the operon XfGUM comprising genes xfgumB, xfgumC, xfgumD, xfgumE, xfgumF, xfgumH, xfgumJ, xfgumK and xfgumM and the uses of such operon, either as DNA as well as the proteins it encodes, for the control of the orange tree disease Citrus Variegated Clorosis (CVC) or related diseases caused by the bacteria in other plants, such as oak trees and grapevines.

The following definition is provided to remove any potential ambiguities as to the intent or scope of their usage in the specification and claims.

"Similarity" as used herein refers to identity of nucleotide sequences. A sequence is said to be 70% similar to another one if, after a global alignment, 70% of the nucleotides of the smaller sequence are identical to the corresponding nucleotides of the other sequence. Global alignments are done by means of dynamic programming (Thompson J D et al. (1997). Nucleic Acids Res. 25, 4876-4882 incorporated by reference). This guarantees a mathematically optimal alignment assigning a value for matches and mismatches between all nucleotides and penalties for insertions or deletions of different lengths. Typical numbers are a score of 1.9 for a match, 0 for a mismatch, for opening a gap and 6.66 for extending this gap.

EXAMPLE 1

A cosmid library was prepared from total DNA of *Xylella fastidiosa*, using standard techniques, including the digestion of the DNA with restriction enzyme BamHI. Those fragments which ranged from about 35-45 kilobases, were selected as being most relevant. A hybridization map was prepared, and reviewed to select the cosmids which did not overlap. Following selection, non-overlapping cosmids were sequenced using the art recognized shotgun approach. One cosmid was selected, in view of similarity to *Xanthomonas* spp. sequences. A fragment of about 12710 nucleotides was isolated, and studied further.

EXAMPLE 2

The further studies referred to in example 1, supra, included comparison of the 12710 nucleotide fragment to the known GUM operon of *Xanthomonas campestris*. The known operon has been described as containing 12 genes; however, the operon disclosed herein appears to contain only nine, i.e., it contains genes with some homology to gumB, C, D, E, F, H, J, K and M; however, no sequences homologous to gumG, I, or L were found.

In order to distinguish the two sets of genes, those which are a part of the invention will be described hereafter as "xfgum" genes, and the operon will be referred to as "XfGUM."

The nucleotide sequences of xfgumB, C, D, E, F, H, J, K and M are set forth as SEQ ID NOS:1-9, respectively. The complete XfGUM operon is set forth at SEQ ID NO:110.

The putative amino acid sequences encoded by the referenced xfgum genes are set forth as SEQ ID NOS:11-19. These were compared to the comparable amino acid sequences for *Xanthomonas campestris*. In FIGS. 1A-1I, homology analysis is presented, using the abbreviations "GUMBXf, GUMCXf," etc., for the proteins of the invention, and "GUMBXc, GUMCXc," etc., for the *X. campestris* proteins.

EXAMPLE 3

The homology of the sequences from *Xylella fastidiosa* to the *Xanthomonas campestris* sequences led to conclusions about the functions of the encoded proteins, and a proposed mechanism for the synthesis of the xanthan-like product by *Xylella fastidiosa*, which is presented in FIG. 2. Specifically, xfgumD encodes a glycosyltransferase I homologue, involved in addition of a first glucose residue via transfer of glucose-1-phosphate from UDP-glucose to an isoprenol phosphate carrier, resulting in the lipid monosaccharide. The next step in the synthesis involves the addition of a second glucose residue via a glycosyltransferase II homologue, encoded by xfgumM, to form a lipid disaccharide. Following this, a glycosyltransferase III homologue encoded by xfgumH is believed to add a mannose residue to form the trisaccharide, after which a glycosyltransferase IV homologue encoded by xfgumK adds a glucouronic acid residue, forming the tetrasaccharide. The xfgumF gene encodes an acetyltransferase I homologue, which catalyzes acetylation of the mannose reside referred to supra. The proteins encoded by xfgumB, C and E appear to be involved in secretion of the xanthan-like EPS through bacterial membranes, while the protein encoded by xfgumJ appears to be involved in the polymerization and secretion of the xanthan-like EPS.

As noted supra, the XfGUM operon lacks components corresponding to *Xanthomonas* syp. genes GUMG, I and L, which encode acetyltransferase II, glucosyltransferase V, and pyruvate transferase. This suggests that the EPS produced by *Xylella fastidiosa* consists of tetrameric units of glucose-glucose-mannose-glucuronic acid, where these tetramers are not pyruvylated, and are acetylated in whole or part.

Hassler, et al., Biotechnol Proj. 6:182-187 (1990), and Levy, et al., Biopolymers 38:251-272 (1996), both indicate that mutant strains of *Xanthanomas*, which are defective in one or more steps of the xanthan biosynthetic pathway synthesize structural variants of xanthans, which had chemical properties that differ from each other and standard xanthans. Both acetylation and pyruvylation are known as processes which affect viscometric properties of xanthan. Pyruvate increases viscosity, and acetate decreases it. Further, when terminal mannose is absent, viscosity decreases. Nonacetylated tetramers lacking side chain terminal mannose have higher viscosity. These prior observations suggest that the EPS described herein will have properties that differ from previously identified xanthans.

The foregoing description, including examples, describes features of the invention. These include isolated nucleic acid molecules which encode any and all of the xfgum proteins described herein, including GUMxfB, C, D, E, F, H, J, K and M, as well as the proteins themselves. Especially preferred are those isolated nucleic acid molecules which comprise or consist of the nucleotide sequences of SEQ ID NOS: 1-9, and nucleic acid molecules which differ therefrom but, in view of the degeneracy of the genetic code, still encode the proteins which have the amino acid sequences set forth in SEQ ID NOS: 11-19.

The isolated nucleic acid molecules of the invention may be included in expression vectors, such that the nucleic acid molecules are in operable linkage with a promoter. In accordance with this feature of the invention, more than one of the nucleic acid molecules described and claimed herein may be included in the expression vector. There are nine nucleic acid molecule families described herein. Any and all combinations of these may be a part of these expression vectors. In other words, combinations of 2, 3, 4, 5, 6, 7, and 8 of the nucleic acid molecules may be a part of these vectors, as well as expression vectors including all 9, or just 1.

Also a part of the invention are recombinant cells, such as recombinant prokaryotic cell strains, and recombinant eukaryotic cell lines, that have been transformed or transfected with one or more of the isolated nucleic acid molecules or recombinant expression vectors of the invention.

Also a part of the invention, as described herein, is the isolated XfGUM operon. A preferred embodiment is that set out in SEQ ID NO: 10; however, it will be understood that the statements regarding the degeneracy of the genetic code referred to supra apply here as well. Further, in connection with the operon, as well as all nucleic acid molecules described herein, principles of preferred codon usage apply in connection with the use of the nucleic acid molecules for transforming or transfecting cells.

As indicated, supra, also a feature of the invention are the proteins encoded by the isolated nucleic acid molecules. These proteins have enzymatic activity, as described herein. Further, they can be used as immunogens to generate antibodies, both polyclonal and monoclonal, which can be used as described infra. Further, these proteins can be produced in various recombinant forms, including fusion proteins, in active forms that consist of less than the entire amino acid sequence of the protein, and so forth. For example, it is well known that enzymes are composed of various structural domains, including one or more active sites. Such active sites are a part of the invention, and comprise less than the entire amino acid sequence of the protein.

As indicated, the proteins of the invention can be used to prepare xanthan like molecules, such as those illustrated in FIG. 2, i.e.:

[glucose-glucose-mannose-glucuronic acid]n.

where n is a whole number from 1 to about 5000, preferably from about 300 to about 5000, most preferably from about 1500-3000.

This structure may be acetylated; however, as indicated supra, when made via a process that comprises the use of the enzymes that are a part of this invention, the resulting tetrasaccharide structure differs from known xanthans in that it is not completely acetylated or pyruvylated. The compounds described, supra, may be polymerized via intracellular or extracellular processes.

The isolation and characterization of the XfGUM operon allows the skilled artisan to determine what substances act as inhibitors or activators of the operon as a whole, or the individual members of the operon. As indicated supra, the xanthan like products of the invention have various industrial uses, and determination of activators and/or agonists permits the artisan to increase production of the materials under appropriate conditions, such as laboratory culture of *Xylella fastidiosa*, or transformed or transfected cells which produce the xanthan like compound. "In the field" at it were, it is desirable to inhibit or antagonize *X. fastidiosa*, and the operon and isolated nucleic acid molecules of the invention permits the artisan to identify materials which are useful in inhibiting the organism.

Other facets of the invention will be clear to the skilled artisan, and need not be elaborated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which comprises a nucleotide sequence which encodes the amino acid sequence which is set forth at SEQ ID NO: 11.

2. The isolated nucleic acid molecule of claim 1, which encodes all of the amino acid sequences which are set forth at SEQ ID NOS: 11, 12, 13, 14, 15, 16, 17, 18, and 19.

3. The isolated nucleic acid molecule of claim 1, comprising the nucleotide sequences set forth at SEQ ID NO: 1.

4. The isolated nucleic acid molecule of claim 1 comprising the nucleotide sequence of SEQ ID NO: 10.

5. An expression vector comprising the isolated nucleic acid molecule of claim 1, operably linked to a promoter.

6. An expression vector comprising the isolated nucleic acid molecule of claim 2, operably linked to a promoter.

7. A recombinant cell transformed or transfected with the isolated nucleic acid molecule of claim 1.

8. A recombinant cell transformed or transfected the isolated nucleic acid molecule of claim 2.

9. A recombinant cell transformed or transfected the expression vector of claim 5.

10. A recombinant cell transformed or transfected the expression vector of claim 6.

* * * * *

SEQUENCE LISTING

```
<160> NUMBER OF SEQ ID NOS: 28

<210> SEQ ID NO 1
<211> LENGTH: 654
<212> TYPE: DNA
<213> ORGANISM: Xyllela fastidiosa
<220> FEATURE:

<400> SEQUENCE: 1

atgtgtacgg ttattctgat ggcttgcaat actgcaccgc attctctggc ctcttctctc      60

ccggtacctg atgcactgct gtttccacaa gtgcagcctg aatacaaagt ttctcctggt     120

gacttattgt tgatcaaggt attccaagtc gatgatctgg agcgtcaggt ccgtgtggac     180

aacactgggc gtattaccct gccattgtta ggaagcattg atgtatccaa taaaggtgcg     240

gctgagttgg aaactctgat agccaatcgt taccgcagtg gctatctgca aaatcctcaa     300

gtttctgttt ttatccaaga agcgaatgca cgccgtgtta ccgtgactgg tgcagtgacc     360
```

-continued gagccgggga gctatccatt gatcggtagc aacctgacat tgcagcaagt gattgctcag 420
gctaaaggta taaacacgct ggcgagtctt caaaacgtgg ttgtattccg tactgtcaaa 480
ggacagaaga tgttggcgcg ctttgatttg gcacgtatcg agcgtggtaa ggatcctgat 540
cctgagatct atcctggtga tctcgttgtt gtttaccgtt ccgacatgcg cttgtttttg 600
cgcactcttg ttgaaattac ccccttcgtt atggtctggc gcgcgtatcg ataa 654

<210> SEQ ID NO 2
<211> LENGTH: 1404
<212> TYPE: DNA
<213> ORGANISM: Xyllela fastidiosa
<220> FEATURE:

<400> SEQUENCE: 2
atggattatc ccaatcaaac ttcttccgct ttgtttcact cctcagaacc attgggtctg 60
aatcttcttg attatttacg tgtgttggtc agtcaatatt ggctgattat tggtgttgcc 120
atcggcgcaa cttcgctagc ccttggtgtc tcgttgctgc ttcctcaaaa gtttcgtgcc 180
actgccacgt tacagattga gcgtgatgtg cctaaggtga tgaatgtcga taatttgatc 240
cctgtagagt cgccgcttga tcgtgatttc tatcaaactc aatatcagtt attacagagt 300
cgttcgttag cgcgtgcagt cattcgtaag atgaacttgg atcgagagcc gatgttgaaa 360
ccactcgtcg ataaagtatt gtcaaaggta caaaatcttc cagttaatac tcgtaacaca 420
gctatcgaga gtgcattgat agaaatgatg ttgaacagtt taaagatcga accgatcctc 480
aattcgaggc tggtctatgt gcattttgat tctcatgatc ccaccttatc ggcgaaggtt 540
gctaatgcct acgccaagat gttcattgaa aataatcagc agcgtcgttc aaatgccttc 600
tcatttgcaa tgaagtatct tgctggacgc ttagaacaat tgcgtatcaa ggtggataag 660
tcagaaagga atgtggttgc gtattccact gatgaaaaga ttgtttctgt gggtgacgaa 720
aaaccatcac tctctgcaca gaacctgagt gatcttaatg cgttgctggc ctccgcacag 780
aatgagcgga ttagggccga agcctcttgg cgtcaggcca gtattggtga tggtctgagt 840
atccctcaag tgttgtctaa cctgttggta cagtctttgc gtaccgagca ggcgaatatg 900
gtcaatgaat atcagcagaa attatccatg tttaaacctg agtatccgga gatgcaacgg 960
ttgaaagcaa gaatcaaaga aaatactaag caaatcaatg ctgaggtatt gaatattagg 1020
caatcgttga agtctcagta tgaagctaca ttacgtcagg agaatctatt gaatgaccgt 1080
attgcagtgt tggagaagga tgagttggat ctgaaaacgc gtcttattcg ttataaccta 1140
ctcgagcgtg aggctgaaac agatcgccaa ctttatgatg cgttgttgca acgttataag 1200
gaaattagtg tgcttggcga tgttggtagt aacaatgtga cggtagtgga tgcggcagat 1260
attccgagcc gcccaatttc gccgaatttg ttaatgaaca cgatattggg tggaattttt 1320
ggtgtctttt tgggtttgac ggttgcgatg gtgcgttatt ccatgcatgg agcgaagcgg 1380
ataaacgtga tgagcgtgga ataa 1404

<210> SEQ ID NO 3
<211> LENGTH: 1455
<212> TYPE: DNA
<213> ORGANISM: Xyllela fastidiosa
<220> FEATURE:

<400> SEQUENCE: 3
atgcttctgg cagatctgaa cagtgttact gatattgctt cttcaccgcg gttattgtcg 60

-continued

```
aaatattctg ctgccgctga tctaatactt cgtgtttttg atctaacaat ggtggtgctc    120

tctggtgtaa tgatttacag attgttgttt ggtacttgga tgttaatggt cccatatcgt    180

attgcgattg gtaacacgtt actgtattcg gtgatttgtt tttctttttt cccgttgtat    240

cgcagttggc gtgggcgtgc tctggcgcgg gagctgttag tacttagtag tgcgttctgt    300

ggtgtattta tcttgttttc gttgcataca ctgattgttc aattgggaca tcctgtctcc    360

tggttatgga ttactttctg gttccttggt gcgctctcta ccttgttgag tgcgcgtgta    420

gcgcttcgta gtctactcaa ctggttgcat atgcgtggtg tggatgtcca acgtattgtt    480

gtggttgggc tgcgtcatcc tgtgatgaaa attcaccatt atctgaatcg taatacatgg    540

acagggatgc aattgattgg gtatttcagt acttcctacg atgtctctgt atctgaatat    600

gtgaggcgtc ttccgtctct tgggacgccg gatagattgt tcgatttttt agaaaaaaat    660

cacgttgagc aagtatggat ttcgatgcct cttggtgagc gtgattatat taagacgttg    720

ttgaagaaat tggagcgtta tccgatcaat gtaaaactta ttcctgattt attcgacttt    780

ggcacactca atcagtcggg tgaacaaatt ggtcatgtgc ctgtcattaa tcttcgtcag    840

ggcggtgttg atcgagataa ctactttttt gttgccaaga caatccagga taaagtgctg    900

gccatgattg cattgctgtt gctgtggccg ttgttaatca tcattgggat tggtatcaag    960

ttcagttccc caggtccggt attgttccgg caacgccgcc atggcttgaa tgggcgtgag   1020

ttttatgtgc tcaaatttcg ttcgatgcgg gtgcatgacg atcaaagtca gcatctgaag   1080

caagccagtc gtaatgacag tcgtatcact gcttttggtg cgttcctgcg tcgcaccagt   1140

ctggatgagt taccacaaat cttcaatgta cttggcggca gtatgtcgat tgttggcccg   1200

cgtcctcatg cggcgcagca caacagttat tacgagaaat tgatccagca ttacatgcaa   1260

cgccattacg tcaaaccagg gattactggg tgggcgcagg tcaacggttt tcgtggtgaa   1320

acacaagaat taaggacaat gaaaaagcgt attcagtacg atcttgatta catccggcgc   1380

tggtcattgt ggttcgattt tcgaattatt gttttgactt tagtacgtgt acttggtcag   1440

aaaaatgctt attga                                                    1455
```

<210> SEQ ID NO 4
<211> LENGTH: 1275
<212> TYPE: DNA
<213> ORGANISM: Xyllela fastidiosa
<220> FEATURE:

<400> SEQUENCE: 4

```
atgctgatgc gtatgagaaa gatcaccaaa gagcattcac ggaatcttct tgttggaata     60

gtgctgtttt ttggagtggc ttataacttt ccgttagcca tgattaacgc caaagttttt    120

acggtgactc cagtgatgac ttatgcagtg gagttggtaa tttattttgc ctgcttcata    180

ctcggattat ctgcattgga tcgcaagcgc gttgtgcttg tgatgagtgg tcttgggttt    240

ctcgttgcat tgacgttgct acggtttctg atgagtttgg attttgatcc aaaattcttc    300

agggatgcgc tgattccatt cgcttttctg atactcggtg cagcctaccg tggatctttg    360

ctgcgtctat tcatgggcat gagtattttt attacttttg ttgctgtttt cgagttgatg    420

atgcctgatg tttatggtga cattgccaat ccgaaaagtt atttcgtgaa ttctcgtggt    480

gctagcgcag acggtttctg gaatgaaggg agtagtttgt atcttagtgc cacgcgtccg    540

gatgagcgta acttctttgc tggttcgaat ttaccacgtg catcttctgt gttcattgaa    600

ccggtgacga tgggaaatta cattatcttt tttgctgcaa ttgtgttggt tttctggcgt    660
```

-continued

```
tggatgagtg tttccgagtt aattttatcg atcgcaatga tcttattttt aattgtcgct    720

tcagatggcc gtttggcgac tggtacatgc atattaatgg tattgcttgc accatttctt    780

aaacgttttg atcagcgttt tgcgtttttg ttattttttt cggtgttact cggtggatgg    840

ttcatagttc aggtgaatgg tattcatgca tatgacaagg atacgattct gagcaggact    900

tttttcagtg tgtattcact ggctcacttg cccttggatt cgtggtttgg cttggatgtt    960

cagtcgtcct atcgttattt tgatagtggt attgcttatt tcatcgcgtc acagtcagtt   1020

atcactgtac ttgttttttt gttggcttat tcatttcttt tcgacatgca aagtcatgag   1080

gggcggggat ttaaaaacat ggccatattc gcatttgcat tgagtctttt ggtatcaaat   1140

agttattttt cgattaaaac gtctgcgttg tggtggttta cgtgtggctg tctttggaat   1200

tgctcgccta aggtattggc tgcaaaaaag aatcttgtag aagcgagagt gatagcacaa   1260

ggaggtgtgt cgtga                                                    1275


<210> SEQ ID NO 5
<211> LENGTH: 1093
<212> TYPE: DNA
<213> ORGANISM: Xyllela fastidiosa
<220> FEATURE:
<221> NAME/KEY: unsure
<222> LOCATION: 562
<223> OTHER INFORMATION: Unknown nucleotide

<400> SEQUENCE: 5

gtgattcatg aaaaaaagta tgtgccagta cgaggaggga cattagcaca ctctccggga     60

tctttatcag ttgggcgtga tgcacgtatt gatgcggcga agggactagg tatttttctg    120

gtagtacttg gtcatgctaa agggcttcca gaatggtggg ttgtgctgat ttacagtttc    180

cacgtgccgt tgtttttcct gttatctggt tgggctgctg gcacgaatat gcgtcagtct    240

ggattctgcg aatgtttgtt gcatttgatg cgtaccttac tggttccata tgtattcttt    300

tttttcgttg gttatatcta ttggttgctt acccgtcata ttggtgcgaa ggatttgcgt    360

tgggggatgc acccttggtg ggagccgttg aatggtttgt tgatgggggg aggaactgct    420

ttgtatgttc atccgtcgtt gtggtttctt ccagcattgt ttgtgacgaa attaacctat    480

caaatgttgt ctaagtatgt ttctttagaa cgattggtgt tgtttggtgg gatattttct    540

tgggtatggg tagggttttt tncctgggtt tggtgtgcgt ttcccatttg ctttagatga    600

attgcctatt gcatttttat ttttcgtttt tggagtgatg ggacgcagaa cgtcttggtt    660

acggttgctc ccgaaaacaa gaaaagcgaa tatgatttta cttgccgtgt tgttgtttcc    720

ttggtttctg ttggcgttgt gcaatgaaaa agttgatatg aatatgctta tttttggcaa    780

ttcaccattt gtttttcatg tttccgcatt gttaggtgtg gcgatagtgt tatgtgcggc    840

ggctcttgtt gagcaatggt cattggtaca atgggctggg cgtaatacgc tgttgatttt    900

gtgcacgcat acgctagttt tttttgtgtt attcggagta ttgtctttgc tcggagggac    960

atctggattg atcttggcat tgctttttttc agcaattacg ttgtgtttta ttccaatttt   1020

tagatggata ttgatgaggt ggataccttg gtcactgggt gcatgttcat atatgcgatc   1080

gcgttcatca tga                                                      1093


<210> SEQ ID NO 6
<211> LENGTH: 1143
<212> TYPE: DNA
<213> ORGANISM: Xyllela fastidiosa
<220> FEATURE:
```

-continued

<400> SEQUENCE: 6
atgaaagtgg tgcatgttgt tcgtcaattt catccgtcaa ttggtgggat ggaggatgtg 60
gtcttcaata ttgcgatgca gctgcatttg catgctggaa tcgatgttga tgtcgtgacg 120
ttgaaccgag tatttactca gtctgatgtt ctacttccat gtactgataa gtatcagggt 180
gtgtcgatcc agcgcattgg ttatcgtggt tcttcgcgtt atccattggc accatgggta 240
ttgcgtatgt tggataaagc cgatgtgatt catgtgcacg gtattgattt tttttatgac 300
tttctggcat tgactcgggt gttacatgga aagccaatgg tcgtttcaac gcacggtggt 360
ttcttccata cggattatgc atcaagactt aaattacttt ggttcaatac gttgactagg 420
ttatcagcgt tggcttatgc aaggattatt gcgagtagtg agagtgatgg tgcgttgttt 480
tcaaagatcg tggcaccgag tcgattgcga gtcattgaaa atggcgtaga tgtggagaag 540
tatgcaaggt gtggtgcttc ggaagctgga cgcactcttt tgtatttcgg gcgctggtcg 600
atgaacaagg gattgttgga gacgttgcaa ttactcgctg tattgtatgt gttagatcca 660
cgctggcgat taattattgc tggacgtgaa tatgattatg atcaggctgc gttggcgtat 720
gaggtggata ggcttgggtt gtctgagcag gtgcattttc attgtagtcc gtcacagtcg 780
cagttgcgct ttttaatgga gcaagcacag ttttttattt cactgtcgcg gcatgagggt 840
tttggtatcg ctgcagttga ggcgatgagt gctggattaa ttcctgtctt gagtgatatt 900
ccaccatttg cgcgtctaca tcgtgagtcc ggtttaggtg ttttggtcga tccattacaa 960
ccacagcagg ctgcagttgc tgtacaggga ttggcagtac aggtagatac tcattttatc 1020
gactggcgat ctcaagcgat ggctttcagt gatcgttatc actggcgtta tgtcattggt 1080
tgttatcagg atgaatattg tagagcgctt ggattaggtg gcgagcagga atttctgagg 1140
tga 1143

<210> SEQ ID NO 7
<211> LENGTH: 1533
<212> TYPE: DNA
<213> ORGANISM: Xyllela fastidiosa
<220> FEATURE:

<400> SEQUENCE: 7
atgagtgaca gtgtggtgag tgtttctgcg gtgtccgagc gtagtttggc ttcacgtgcg 60
cttggcggtg ccgtggtgac gatgcttggg caggggggcga gggtagttat ccaattttcc 120
attatcgtgc tattggcgcg gttgttgaat ccgcatgatt atggtctgat ggcgatggtc 180
actgcgattg tgggtgttgc tgatattctt cgtgattttg gcctttcttc ggcggcgatc 240
caggccaagc agattacaaa cgcgcagcgc gataatctat tctggattaa tagtgtgatc 300
ggattggcac tgtcgttggt ggtattcgtt gcggcacagc taattgctga tttttatcgt 360
gaacctgcat tagtgacgat tacgcaggta ttggcgatta attttttact taatgggatg 420
gcaactcagt atcgcgccaa tcttagccgt gagatgcgtt tcggtcagct tgcattgagt 480
gatattggtg cgcaggtgtt aggtctgtta gttggtgtta gtgtggcgct ggtcggatgg 540
ggcgtttggg cgttggtgtt gcagcaggtg gtgcaagctg tggcgaatct ggtaattgca 600
atggtctgtg cgcgttggct gccaggtggt tatcgccgtg gtgtgccgat ggggagtttt 660
ctcagttttg gttggaatct gatggttgcg caattgctaa gctatgccaa tcgcagtgtt 720
ggtcaagtga ttatcggtta tcggcttggt cctaatgtac ttggtttgta taaccgtgca 780
ttccagttgt tgatgatgcc attgaatcag gtgattgcac cggcaagttc agtggcgttg 840

-continued

```
ccggtgcttt ctcagttgca agatgatcgt gctcgtttcg atagcttctt attgcgtggg     900

caaacgatga tgttgcatgt gattgttgcg ttgtttgcat tttcttgtgc gcaggccact     960

ccattaattg tattggtcct tggtgaaaag tggcgttcgg cggtgttgtt attccaaatt    1020

ctgacattgg ctggtatgac gcagagtgcg agttatgcaa gttattggct atttttagca    1080

cgcggtttga tacgcgatca tcttttattt tctattgtca gtcatgtgtt tttggtgttg    1140

tgtgtgtgca ttggtgctta ttggggtgta tttggtgtcg ctattggtta cagcattagt    1200

ttagctttga tatggccatt gtcgattatt tgggcggcgc gtattacacc tgttcctggt    1260

tgggaaatgt ttttcaatgg gatgcgtgcg atcgtaggtt acggggtgtg tgcattcgct    1320

tctatgtatg cttcgcagtg gtgtgacgag tcgaatcttt ggaagcaatt gatagttggt    1380

gctttggcaa tgttggtagc ttttgcagtg ttatccttgt tatggtcagc atttcgtcgt    1440

gatgtgctgt ctatcattaa gatcggtatg tcttcttcag tagtatcttc ttttcttcta    1500

aggatcatga ggagagtgag gaagggatct taa                                 1533
```

<210> SEQ ID NO 8
<211> LENGTH: 846
<212> TYPE: DNA
<213> ORGANISM: Xyllela fastidiosa
<220> FEATURE:

<400> SEQUENCE: 8

```
atgctctttc gctggtatgt gcagcatcca ccggagattt tattgcagtg gatacgcgaa      60

gcagacatca ttttgttcga gagtggtact gcagttgcgt tcattgatat ggcgaagcgt     120

attaatccat ctgcccgtct tatttataat gcttcagata gtctcagtgc gattaatgta     180

gcatgttata tcgagcgtga atttcagcgg gttgctgcaa gtttggatgt gatcgctgtt     240

gtttctcctg cgatgactaa agaaattcct agtcatggca atgtgtttta tatcggccat     300

ggggttcttc aaaatttgag tgagcttggt ggtccatcgc catatgaggg tgggatccat     360

gccgtatcgg ttggttcgat gttgtttgat ccgttatttt ttgtggttgc agggaaggag     420

tttccacata ttacttttca tgttatcggt tcagggatgg ggcggcatcc tgattatcct     480

gataatgtcg tggtttacgg tgagatgaag tacgttgaaa ctattcgtta tattaggcat     540

gcatctttcg gtattgcgcc gtatgtgtca cagcaggttc cagaatattt agccgatagt     600

tcgatgaaac tgttgcagta cgactttttc gggttaccgg cagtgtgtcc gcatgcggtg     660

gtcggctctt atccgacacg ctttggttat actccaggga atgctattga gttggtggct     720

gcgatcaagc gtgcgttgca agcgccgcat cagcagtctc gtcaatattt gagttgggaa     780

gaggttgttg ctcgtgtttt ggatcctact gcctatgagg gaacccggat attacctgcg     840

gtgtga                                                                846
```

<210> SEQ ID NO 9
<211> LENGTH: 798
<212> TYPE: DNA
<213> ORGANISM: Xyllela fastidiosa
<220> FEATURE:

<400> SEQUENCE: 9

```
gtgtgggctt ttggagactt tgttgtgacg atctctggca tttcttccga tccacccttc      60

attgaaacga ttgatactct gttgcttggt gggtttccgg tgttatcaac cacgccgtct     120

gcctttgttg cttcgctgta ccgtagtttg actgaagaaa gaccgcagcg ggtatttttt     180

gctaatacaa attttatcgt gcaatgccag tcgctccggg ggcggatgta ttcggagcgg     240
```

-continued

```
gtttgtatcc tcaacgatgg gataggcatg gatttggctg cgctgttcat tcatggtcgt    300
cgttttgtta gtaatctgaa tggtactgat ttgatcccgt atctatgtca gcacgctcca    360
cgtccgttgc gctttttctt gcttggtgcc aagcctggtg ttgccgatat ggcggcgcag    420
acgttgtgtc agttggggca attagtggtc ggtacttgtg atgggtatgc gcagttcatt    480
gcggctggtg aggatttagt tgagtcaatt aatgccagcg gtgccgatgt gttgttggtt    540
gctttgggta atcctgtgca ggagcgttgg attcttgatc atgatgtgca gttgcataca    600
ccattggttt ttggtgttgg tgcgttgttt gattttatgt ctggtaatgt gcggcgtgcg    660
cctttatggg tacgtcgtgt acgtggtgaa tggttgtacc gattgttgtt ggagccaaga    720
cgtttattta aacgctacag ttgggatctg cttcggtttt ttggtgtgtg tttattacgg    780
cgaagggggg tgaattaa                                                  798
```

<210> SEQ ID NO 10
<211> LENGTH: 12704
<212> TYPE: DNA
<213> ORGANISM: Xyllela fastidiosa
<220> FEATURE:

<400> SEQUENCE: 10

```
aaaacaccat aacctcgaaa aaaccataca ccgccccgat caccagcgat tatctcctca     60
ctgaatatcg gctccatctt tgataataaa aaacacaact attatttcga tcattacaca    120
ccgagtatca acaccagaga cgtaacaaag caggacaaca acatcttgaa acgcatacat    180
caatactgat aaataaaaaa tcagacaaca cgcaaattaa ttcacccccc ttcgccgtaa    240
taaacacaca ccaaaaaacc gaagcagatc ccaactgtag cgtttaaata aacgtcttgg    300
ctccaacaac aatcggtaca accattcacc acgtacacga cgtacccata aggcgcacgc    360
cgcacattac cagacataaa atcaaacaac gcaccaacac caaaaaccaa tggtgtatgc    420
aactgcacat catgatcaag aatccaacgc tcctgcacag gattacccaa agcaaccaac    480
aacacatcgg caccgctggc attaattgac tcaactaaat cctcaccagc cgcaatgaac    540
tgcgcatacc catcacaagt accgaccact aattgcccca actgacacaa cgtctgcgcc    600
gccatatcgg caacaccagg cttggcacca agcaagaaaa agcgcaacga cgtggagcgt    660
gctgacatag atacgggatc aaatcagtac cattcagatt actaacaaaa cgacgaccat    720
gaatgaacag cgcagccaaa tccatgccta tcccatcgtt gaggatacaa acccgctccg    780
aatacatccg cccccggagc gactggcatt gcacgataaa atttgtatta gcaaaaaata    840
cccgctgcgg tctttcttca gtcaaactac ggtacagcga agcaacaaag gcagacggcg    900
tggttgataa caccggaaac ccaccaagca acagagtatc aatcgtttca atgaagggtg    960
gatcggaaga aatgccagag atcgtcacaa caaagtctcc aaaagcccac accgcagtac   1020
gggaaaatca tcaacagtaa agatgactcc acacgtttaa acacacctca caccttctat   1080
agagacacta aagttatgca tcaactttcg ctccttcacc accaataatg aaaaataaaa   1140
ctacggatac agatacgctc acaccgcagg taatatccgg gttccctcat aggcagtagg   1200
atccaaaaca cgagcaacaa cctcttccca actcaaatat tgacgagact gctgatgcgg   1260
cgcttgcaac gcacgcttga tcgcagccac caactcaata gcattccctg gagtataacc   1320
aaagcgtgtc ggataagagc cgaccaccgc atgcggacac actgccggta acccgaaaaa   1380
gtcgtactgc aacagtttca tcgaactatc ggctaaatat tctggaacct gctgtgacac   1440
atacggcgca ataccgaaag atgcatgcct aatataacga atagtttcaa cgtacttcat   1500
```

-continued

```
ctcaccgtaa accacgacat tatcaggata atcaggatgc cgccccatcc ctgaaccgat   1560
aacatgaaaa gtaatatgtg gaaactcctt ccctgcaacc acaaaaaata acggatcaaa   1620
caacatcgaa ccaaccgata cggcatggat cccaccctca tatggcgatg gaccaccaag   1680
ctcactcaaa ttttgaagaa ccccatggcc gatataaaac acattgccat gactaggaat   1740
ttctttagtc atcgcaggag aaacaacagc gatcacatcc aaacttgcag caaccccgctg  1800
aaattcacgc tcgatataac atgctacatt aatcgcactg agactatctg aagcattata   1860
aataagacgg gcagatggat taatacgctt cgccatatca atgaacgcaa ctgcagtacc   1920
actctcgaac aaaatgatgt ctgcttcgcg tatccactgc aataaaatct ccggtggatg   1980
ctgcacatac cagcgaaaga gcatatcctc aataccacgc aaccatgatc tacgtgtatt   2040
aaacggatgt accaacgtac gccatagata acaatgcaca ccattatact caaccacatg   2100
attagcatac tcatccaacg ggacacgcaa atcttttttt agcctggaca acaaactgta   2160
acgtaatgag aaaaaacgag tatcaccacg cttagccaat tcatccgtaa tgaaatgaat   2220
actggcacga cgtggtgtac gataatcatg cgctgacaaa accagataat tgggacgcac   2280
tccaacggac atcgtagaaa catttgcatc gtggcttaat accgcacttg tagaagcatt   2340
cataagctcg ctcgttattc actgaattaa cgtattccat taattttcaa aaaaatccta   2400
agaaccgatg aattaagatc ccttcctcac tctcctcatg atccttagaa gaaaagaaga   2460
tactactgaa gaagacatac cgatcttaat gatagacagc acatcacgac gaaatgctga   2520
ccataacaag gataacactg caaaagctac caacattgcc aaagcaccaa ctatcaattg   2580
cttccaaaga ttcgactcgt cacaccactg cgaagcatac atagaagcga atgcacacac   2640
cccgtaacct acgatcgcac gcatcccatt gaaaaacatt tcccaaccag gaacaggtgt   2700
aatacgcgcc gcccaaataa tcgacaatgg ccatatcaaa gctaaactaa tgctgtaacc   2760
aatagcgaca ccaaatacac cccaataagc accaatgcac acacacaaca ccaaaaacac   2820
atgactgaca atagaaaata aaagatgatc gcgtatcaaa ccgcgtgcta aaaatagcca   2880
ataacttgca taactcgcac tctgcgtcat accagccaat gtcagaattt ggaataacaa   2940
caccgccgaa cgccactttt caccaaggac caatacaatt aatggagtgg cctgcgcaca   3000
agaaaatgca aacaacgcaa caatcacatg caacatcatc gtttgcccac gcaataagaa   3060
gctatcgaaa cgagcacgat catcttgcaa ctgagaaagc accggcaacg ccactgaact   3120
tgccggtgca atcacctgat tcaatggcat catcaacaac tggaatgcac ggttatacaa   3180
accaagtaca ttaggaccaa gccgataacc gataatcact tgaccaacac tgcgattggc   3240
atagcttagc aattgcgcaa ccatcagatt ccaaccaaaa ctgagaaaac tccccatcgg   3300
cacaccacgg cgataaccac ctggcagcca acgcgcacag accattgcaa ttaccagatt   3360
cgccacagct tgcaccacct gctgcaacac caacgcccaa acgccccatc cgaccagcgc   3420
cacactaaca ccaactaaca gacctaacac ctgcgcacca atatcactca atgcaagctg   3480
accgaaacgc atctcacggc taagattggc gcgatactga gttgccatcc cattaagtaa   3540
aaaattaatc gccaatacct gcgtaatcgt cactaatgca ggttcacgat aaaaatcagc   3600
aattagctgt gccgcaacga ataccaccaa cgacagtgcc aatccgatca cactattaat   3660
ccagaataga ttatcgcgct gcgcgtttgt aatctgcttg gcctggatcg ccgccgaaga   3720
aaggccaaaa tcacgaagaa tatcagcaac acccacaatc gcagtgacca tcgccatcag   3780
accataatca tgcggattca acaaccgcgc caatagcacg ataatggaaa attggataac   3840
```

-continued

```
taccctcgcc ccctgcccaa gcatcgtcac cacggcaccg ccaagcgcac gtgaagccaa   3900
actacgctcg gacaccgcag aaacactcac cacactgtca ctcatatcat caccttatcc   3960
ctgtgccaca gcacctgaac taaacacgac atcggcaaca tccattcaat gtaactgagg   4020
catagcatcc acaatgcccc aagcatatag tgcaacaacg cattaatccg cctggattga   4080
ctatcgatat tcccaagatt cttacagaaa ttcacaatcc aaaaattggt aacgacacat   4140
acatcaatca tccgatttag ctgcatactc aacagaccgc gatacctgcg taatatttta   4200
tgcattaaga aatcatgcac ctgtgaaaaa aaatttattc gccaccaata gtgctccact   4260
gaaaaaaacc tattcaatcg cttcgacata ctggaaacaa cccaaaacaa aaagacacca   4320
ttcacctcag aaattcctgc tcgccaccta atccaagcgc tctacaatat tcatcctgat   4380
aacaaccaat gacataacgc cagtgataac gatcactgaa agccatcgct tgagatcgcc   4440
agtcgataaa atgagtatct acctgtactg ccaatccctg tacagcaact gcagcctgct   4500
gtggttgtaa tggatcgacc aaaacaccta aaccggactc acgatgtaga cgcgcaaatg   4560
gtggaatatc actcaagaca ggaattaatc cagcactcat cgcctcaact gcagcgatac   4620
caaaaccctc atgccgcgac agtgaaataa aaaactgtgc ttgctccatt aaaaagcgca   4680
actgcgactg tgacggacta caatgaaaat gcacctgctc agacaaccca agcctatcca   4740
cctcatacgc caacgcagcc tgatcataat catattcacg tccagcaata attaatcgcc   4800
agcgtggatc taacacatac aatacagcga gtaattgcaa cgtctccaac aatcccttgt   4860
tcatcgacca gcgcccgaaa tacaaaagag tgcgtccagc ttccgaagca ccacaccttg   4920
catacttctc cacatctacg ccattttcaa tgactcgcaa tcgactcggt gccacgatct   4980
ttgaaaacaa cgcaccatca ctctcactac tcgcaataat ccttgcataa gccaacgctg   5040
ataacctagt caacgtattg aaccaaagta atttaagtct tgatgcataa tccgtatgga   5100
agaaaccacc gtgcgttgaa acgaccattg gctttccatg taacacccga gtcaatgcca   5160
gaaagtcata aaaaaaatca ataccgtgca catgaatcac atcggcttta tccaacatac   5220
gcaataccca tggtgccaat ggataacgcg aagaaccacg ataaccaatg cgctggatcg   5280
acacaccctg atacttatca gtacatggaa gtagaacatc agactgagta aatactcggt   5340
tcaacgtcac gacatcaaca tcgattccag catgcaaatg cagctgcatc gcaatattga   5400
agaccacatc ctccatccca ccaattgacg gatgaaattg acgaacaaca tgcaccactt   5460
tcattaaaca gtgctcccat tccattcaaa attacaaaga ttcgaatgat ccccactgaa   5520
tgcaacaagt cataattttt tgataaatca aaaaattatg gttccaagga taagaacatc   5580
attttcaata acacaacaac atccttagcc ataacggatt cgactttggt atgaaactcc   5640
ctagaacaaa tcaccaacct attattaatg aataaaaaag acattcctta aaaataataa   5700
aatatctaaa tacctattat acctataaca taaaaaaaca aatgcactgc tcatcgaaaa   5760
tacgaaaaac catgccgcca cagcggatta ttaaaatcca acacaacata aaaacaccac   5820
atcacctaaa agcgacacta attagagatc catcacatcc agataaaact cacatcatga   5880
tgaacgcgat cgcatatatg aacatgcacc cagtgaccaa ggtatccacc tcatcaatat   5940
ccatctaaaa attggaataa aacacaacgt aattgctgaa aaaagcaatg ccaagatcaa   6000
tccagatgtc cctccgagca aagacaatac tccgaataac acaaaaaaaa ctagcgtatg   6060
cgtgcacaaa atcaacagcg tattacgccc agcccattgt accaatgacc attgctcaac   6120
aagagccgcc gcacataaca ctatcgccac acctaacaat gcggaaacat gaaaaaaaat   6180
ggtgaattgc caaaaataag catattcata tcaacttttt cattgcacaa cgccaacaga   6240
```

-continued

```
aaccaaggaa acaacaacac ggcaagtaaa atcatattcg cttttcttgt tttcgggagc   6300
aaccgtaacc aagacgttct gcgtcccatc actccaaaaa cgaaaaataa aaatgcaata   6360
ggcaattcat ctaaagcaaa tgggaaacgc acaccaaacc caggaaaaaa ccctacccat   6420
acccaagaaa atatcccacc aaacaacacc aatcgttcta aagaaacata cttagacaac   6480
atttgatagg ttaatttcgt cacaaacaat gctggaagaa accacaacga cggatgaaca   6540
tacaaagcag ttcctccccc catcaacaaa ccattcaacg gctcccacca agggtgcatc   6600
ccccaacgca aatccttcgc accaatatga cgggtaagca accaatagat ataaccaacg   6660
aaaaaaaaga atacatatgg aaccagtaag gtacgcatca aatgcaacaa acattcgcag   6720
aatccagact gacgcatatt cgtgccagca gcccaaccag ataacagaaa aaacaacggc   6780
acgtggaaac tgtaaatcag cacaacccac cattctggaa gccctttagc atgaccaagt   6840
actaccagaa aaatacctag tcccttcgcc gcatcaatac gtgcatcacg cccaactgat   6900
aaagatcccg gagagtgtgc taatgtccct cctcgtactg gcacatactt tttttcatga   6960
atcacgacac acctccttgt gctatcactc tcgcttctac aagattcttt tttgcagcca   7020
ataccttagg cgagcaattc caaagacagc cacacgtaaa ccaccacaac gcagacgttt   7080
taatcgaaaa ataactattt gataccaaaa gactcaatgc aaatgcgaat atggccatgt   7140
ttttaaatcc ccgcccctca tgactttgca tgtcgaaaag aaatgaataa gccaacaaaa   7200
aaacaagtac agtgataact gactgtgacg cgatgaaata agcaatacca ctatcaaaat   7260
aacgatagga cgactgaaca tccaagccaa accacgaatc caagggcaag tgagcagtga   7320
atacacactg aaaaaagtcc tgctcagaat cgtatccttg tcatatgcat gaataccatt   7380
cacctgaact atgaaccatc caccgagtaa caccgaaaaa aataacaaaa acgcaaaacg   7440
ctgatcaaaa cgtttaagaa atggtgcaag caataccatt aatatgcatg taccagtcgc   7500
caaacggcca tctgaagcga caattaaaaa taagatcatt gcgatcgata aaattaactc   7560
ggaaacactc atccaacgcc agaaaaccaa cacaattgca gcaaaaaaga taatgtaatt   7620
tcccatcgtc accggttcaa tgaacacaga agatgcacgt ggtaaattcg aaccagcaaa   7680
gaagttacgc tcatccggac gcgtggcact aagatacaaa ctactccctt cattccagaa   7740
accgtctgcg ctagcaccac gagaattcac gaaataactt ttcggattgg caatgtcacc   7800
ataaacatca ggcatcatca actcgaaaac agcaacaaaa gtaataaaaa tactcatgcc   7860
catgaataga cgcagcaaag atccacggta ggctgcaccg agtatcagaa aagcaatgga   7920
atcagcgcat ccctgaagaa ttttggatca aaatccaaac tcatcagaaa ccgtagcaac   7980
gtcaatgcaa cgagaaaccc aagaccactc atcacaagca caacgcgctt gcgatccaat   8040
gcagataatc cgagtatgaa gcaggcaaaa taaattacca actccactgc ataagtcatc   8100
actggagtca ccgtaaaaac tttggcgtta atcatggcta acggaaagtt ataagccact   8160
ccaaaaaaca gcactattcc aacaagaaga ttccgtgaat gctctttggt gatctttctc   8220
atacgcatca gcatggaaac tctcctgaca cagccatgca tggactgaaa catctaagat   8280
caataagcat ttttctgacc aagtacacgt actaaagtca aaacaataat tcgaaaatcg   8340
aaccacaatg accagcgccg gatgtaatca agatcgtact gaatacgctt tttcattgtc   8400
cttaattctt gtgtttcacc acgaaaaccg ttgacctgcg cccacccagt aatccctggt   8460
ttgacgtaat ggcgttgcat gtaatgctgg atcaatttct cgtaataact gttgtgctgc   8520
gccgcatgag gacgcgggcc aacaatcgac atactgccgc caagtacatt gaagatttgt   8580
```

-continued

```
ggtaactcat ccagactggt gcgacgcagg aacgcaccaa aagcagtgat acgactgtca   8640
ttacgactgg cttgcttcag atgctgactt tgatcgtcat gcacccgcat cgaacgaaat   8700
ttgagcacat aaaactcacg cccattcaag ccatggcggc gttgccggaa caataccgga   8760
cctggggaac tgaacttgat accaatccca atgatgatta acaacggcca cagcaacagc   8820
aatgcaatca tggccagcac tttatcctgg attgtcttgg caacaaaaaa gtagttatct   8880
cgatcaacac cgccctgacg aagattaatg acaggcacat gaccaatttg ttcacccgac   8940
tgattgagtg tgccaaagtc gaataaatca ggaataagtt ttacattgat cggataacgc   9000
tccaatttct tcaacaacgt cttaatataa tcacgctcac caagaggcat cgaaatccat   9060
acttgctcaa cgtgattttt ttctaaaaaa tcgaacaatc tatccggcgt cccaagagac   9120
ggaagacgcc tcacatattc agatacagag acatcgtagg aagtactgaa atacccaatc   9180
aattgcatcc ctgtccatgt attacgattc agataatggt gaattttcat cacaggatga   9240
cgcagcccaa ccacaacaat acgttggaca tccacaccac gcatatgcaa ccagttgagt   9300
agactacgaa gcgctacacg cgcactcaac aaggtagaga gcgcaccaag gaaccagaaa   9360
gtaatccata accaggagac aggatgtccc aattgaacaa tcagtgtatg caacgaaaac   9420
aagataaata caccacagaa cgcactacta agtactaaca gctcccgcgc cagagcacgc   9480
ccacgccaac tgcgatacaa cgggaaaaaa gaaaaacaaa tcaccgaata cagtaacgtg   9540
ttaccaatcg caatacgata tgggaccatt aacatccaag taccaaacaa caatctgtaa   9600
atcattacac cagagagcac caccattgtt agatcaaaaa cacgaagtat tagatcagcg   9660
gcagcagaat atttcgacaa taaccgcggt gaagaagcaa tatcagtaac actgttcaga   9720
tctgccagaa gcattgatag aactcctcac atatcctggg cagcgcatat tgtgggagga   9780
acaagcgcgc accaccagac aacgttggtt tcgttcacca gcatttgcca ccatgcatca   9840
atccctaaca aacgccggca ctttacttaa aaggaatctg accaccaagc atcagaacta   9900
aatcaatgaa aaccgcctgc tacacttcac tcaatacaac tgcctttatt ccacgctcat   9960
cacgtttatc cgcttcgctc catgcatgga ataacgcacc atcgcaaccg tcaaacccaa  10020
aaagacacca aaaattccac ccaatatcgt gttcattaac aaattcggcg aaattgggcg  10080
gctcggaata tctgccgcat ccactaccgt cacattgtta ctaccaacat cgccaagcac  10140
actaatttcc ttataacgtt gcaacaacgc atcataaagt tggcgatctg tttcagcctc  10200
acgctcgagt aggttataac gaataagacg cgttttcaga tccaactcat ccttctccaa  10260
cactgcaata cggtcattca atagattctc ctgacgtaat gtagcttcat actgagactt  10320
caacgattgc ctaatattca atacctcagc attgatttgc ttagtatttt ctttgattct  10380
tgctttcaac cgttgcatct ccggatactc aggtttaaac atggataatt tctgctgata  10440
ttcattgacc atattcgcct gctcggtacg caaagactgt accaacaggt tagacaacac  10500
ttgagggata ctcagaccat caccaatact ggcctgacgc caagaggctt cggccctaat  10560
ccgctcattc tgtgcggagg ccagcaacgc attaagatca ctcaggttct gtgcagagag  10620
tgatggtttt tcgtcaccca cagaaacaat cttttcatca gtggaatacg caaccacatt  10680
cctttctgac ttatccacct tgatacgcaa ttgttctaag cgtccagcaa gatacttcat  10740
tgcaaatgag aaggcatttg aacgacgctg ctgattattt tcaatgaaca tcttggcgta  10800
ggcattagca accttcgccg ataaggtggg atcatgagaa tcaaaatgca catagaccag  10860
cctcgaattg aggatcggtt cgatctttaa actgttcaac atcatttcta tcaatgcact  10920
ctcgatagct gtgttacgag tattaactgg aagattttgt acctttgaca atactttatc  10980
```

-continued

```
gacgagtggt ttcaacatcg gctctcgatc caagttcatc ttacgaatga ctgcacgcgc  11040
taacgaacga ctctgtaata actgatattg agtttgatag aaatcacgat caagcggcga  11100
ctctacaggg atcaaattat cgacattcat caccttaggc acatcacgct caatctgtaa  11160
cgtggcagtg gcacgaaact tttgaggaag cagcaacgag acaccaaggg ctagcgaagt  11220
tgcgccgatg gcaacaccaa taatcagcca atattgactg accaacacac gtaaataatc  11280
aagaagattc agacccaatg gttctgagga gtgaaacaaa gcggaagaag tttgattggg  11340
ataatccata gttatcgata cgcgcgccag accataacga aggggtaat ttcaacaaga  11400
gtgcgcaaaa acaagcgcat gtcggaacgg taaacaacaa cgagatcacc aggatagatc  11460
tcaggatcag gatccttacc acgctcgata cgtgccaaat caaagcgcgc caacatcttc  11520
tgtcctttga cagtacggaa tacaaccacg ttttgaagac tcgccagcgt gtttatacct  11580
ttagcctgag caatcacttg ctgcaatgtc aggttgctac cgatcaatgg atagctcccc  11640
ggctcggtca ctgcaccagt cacggtaaca cggcgtgcat tcgcttcttg gataaaaaca  11700
gaaacttgag gattttgcag atagccactg cggtaacgat tggctatcag agtttccaac  11760
tcagccgcac ctttattgga tacatcaatg cttcctaaca atggcagggt aatacgccca  11820
gtgttgtcca cacggacctg acgctccaga tcatcgactt ggaatacctt gatcaacaat  11880
aagtcaccag gagaaacttt gtattcaggc tgcacttgtg gaaacagcag tgcatcaggt  11940
accgggagag aagaggccag agaatgcggt gcagtattgc aagccatcag aataaccgta  12000
cacattaagg acaaactcac tagtcccgtt aatttcatac gcgatgacat gaacctcttg  12060
tagggaaaaa tcgagtaatg gctcgccata tcgtcccgat gcaaatagaa acggataaaa  12120
aattgaaaca attcgccaaa cacattttgc ataaagtatc gagatacaac ttttaactat  12180
ttctaactat cgcataggag atgcgcagtg caatctttat tgaactattt tttgggagat  12240
tcttgacgga gttggctcaa tgaatagatt tttataggca ctcaaaactt gaggttgcct  12300
cctaatacac cgccactctg aattgcatct tttttgatgc tcgactcatc agggaaccat  12360
gcaacaaaca tgcccccaca taaagaaata tcagggaatc tgataacccg atgaggatat  12420
acaactcata ttgcatcggc atgagtgcat gaattcgagc aacatcaatt acagactgtg  12480
aaataaatag caatacacgc ctttctcaat gagaaagatc gcaacaatca cggcattcag  12540
caactaaaca tcatactttc tgaaacacac atataaaaaa gcgtgcttta atataaaaat  12600
tattgatgcc ataacttaag caatcggcat tgggctacag caatattgca tgtagcccat  12660
agaagaaaac tagcgtttat caaaccacac tgattaatac gact                   12704
```

```
<210> SEQ ID NO 11
<211> LENGTH: 217
<212> TYPE: PRT
<213> ORGANISM: Xyllela fastidiosa
<220> FEATURE:

<400> SEQUENCE: 11

Met Cys Thr Val Ile Leu Met Ala Cys Asn Thr Ala Pro His Ser Leu
  1             5                  10                  15

Ala Ser Ser Leu Pro Val Pro Asp Ala Leu Leu Phe Pro Gln Val Gln
            20                  25                  30

Pro Glu Tyr Lys Val Ser Pro Gly Asp Leu Leu Leu Ile Lys Val Phe
        35                  40                  45

Gln Val Asp Asp Leu Glu Arg Gln Val Arg Val Asp Asn Thr Gly Arg
    50                  55                  60
```

-continued

```
Ile Thr Leu Pro Leu Leu Gly Ser Ile Asp Val Ser Asn Lys Gly Ala
65                  70                  75                  80

Ala Glu Leu Glu Thr Leu Ile Ala Asn Arg Tyr Arg Ser Gly Tyr Leu
                85                  90                  95

Gln Asn Pro Gln Val Ser Val Phe Ile Gln Glu Ala Asn Ala Arg Arg
            100                 105                 110

Val Thr Val Thr Gly Ala Val Thr Glu Pro Gly Ser Tyr Pro Leu Ile
        115                 120                 125

Gly Ser Asn Leu Thr Leu Gln Gln Val Ile Ala Gln Ala Lys Gly Ile
    130                 135                 140

Asn Thr Leu Ala Ser Leu Gln Asn Val Val Val Phe Arg Thr Val Lys
145                 150                 155                 160

Gly Gln Lys Met Leu Ala Arg Phe Asp Leu Ala Arg Ile Glu Arg Gly
                165                 170                 175

Lys Asp Pro Asp Pro Glu Ile Tyr Pro Gly Asp Leu Val Val Val Tyr
            180                 185                 190

Arg Ser Asp Met Arg Leu Phe Leu Arg Thr Leu Val Glu Ile Thr Pro
        195                 200                 205

Phe Val Met Val Trp Arg Ala Tyr Arg
    210                 215


<210> SEQ ID NO 12
<211> LENGTH: 467
<212> TYPE: PRT
<213> ORGANISM: Xyllela fastidiosa
<220> FEATURE:

<400> SEQUENCE: 12

Met Asp Tyr Pro Asn Gln Thr Ser Ser Ala Leu Phe His Ser Ser Glu
1               5                   10                  15

Pro Leu Gly Leu Asn Leu Leu Asp Tyr Leu Arg Val Leu Val Ser Gln
            20                  25                  30

Tyr Trp Leu Ile Ile Gly Val Ala Ile Gly Ala Thr Ser Leu Ala Leu
        35                  40                  45

Gly Val Ser Leu Leu Leu Pro Gln Lys Phe Arg Ala Thr Ala Thr Leu
    50                  55                  60

Gln Ile Glu Arg Asp Val Pro Lys Val Met Asn Val Asp Asn Leu Ile
65                  70                  75                  80

Pro Val Glu Ser Pro Leu Asp Arg Asp Phe Tyr Gln Thr Gln Tyr Gln
                85                  90                  95

Leu Leu Gln Ser Arg Ser Leu Ala Arg Ala Val Ile Arg Lys Met Asn
            100                 105                 110

Leu Asp Arg Glu Pro Met Leu Lys Pro Leu Val Asp Lys Val Leu Ser
        115                 120                 125

Lys Val Gln Asn Leu Pro Val Asn Thr Arg Asn Thr Ala Ile Glu Ser
    130                 135                 140

Ala Leu Ile Glu Met Met Leu Asn Ser Leu Lys Ile Glu Pro Ile Leu
145                 150                 155                 160

Asn Ser Arg Leu Val Tyr Val His Phe Asp Ser His Asp Pro Thr Leu
                165                 170                 175

Ser Ala Lys Val Ala Asn Ala Tyr Ala Lys Met Phe Ile Glu Asn Asn
            180                 185                 190

Gln Gln Arg Arg Ser Asn Ala Phe Ser Phe Ala Met Lys Tyr Leu Ala
        195                 200                 205
```

-continued

```
Gly Arg Leu Glu Gln Leu Arg Ile Lys Val Asp Lys Ser Glu Arg Asn
    210                 215                 220

Val Val Ala Tyr Ser Thr Asp Glu Lys Ile Val Ser Val Gly Asp Glu
225                 230                 235                 240

Lys Pro Ser Leu Ser Ala Gln Asn Leu Ser Asp Leu Asn Ala Leu Leu
                245                 250                 255

Ala Ser Ala Gln Asn Glu Arg Ile Arg Ala Glu Ala Ser Trp Arg Gln
            260                 265                 270

Ala Ser Ile Gly Asp Gly Leu Ser Ile Pro Gln Val Leu Ser Asn Leu
        275                 280                 285

Leu Val Gln Ser Leu Arg Thr Glu Gln Ala Asn Met Val Asn Glu Tyr
    290                 295                 300

Gln Gln Lys Leu Ser Met Phe Lys Pro Glu Tyr Pro Glu Met Gln Arg
305                 310                 315                 320

Leu Lys Ala Arg Ile Lys Glu Asn Thr Lys Gln Ile Asn Ala Glu Val
                325                 330                 335

Leu Asn Ile Arg Gln Ser Leu Lys Ser Gln Tyr Glu Ala Thr Leu Arg
            340                 345                 350

Gln Glu Asn Leu Leu Asn Asp Arg Ile Ala Val Leu Glu Lys Asp Glu
        355                 360                 365

Leu Asp Leu Lys Thr Arg Leu Ile Arg Tyr Asn Leu Leu Glu Arg Glu
    370                 375                 380

Ala Glu Thr Asp Arg Gln Leu Tyr Asp Ala Leu Leu Gln Arg Tyr Lys
385                 390                 395                 400

Glu Ile Ser Val Leu Gly Asp Val Gly Ser Asn Asn Val Thr Val Val
                405                 410                 415

Asp Ala Ala Asp Ile Pro Ser Arg Pro Ile Ser Pro Asn Leu Leu Met
            420                 425                 430

Asn Thr Ile Leu Gly Gly Ile Phe Gly Val Phe Leu Gly Leu Thr Val
        435                 440                 445

Ala Met Val Arg Tyr Ser Met His Gly Ala Lys Arg Ile Asn Val Met
    450                 455                 460

Ser Val Glu
465


<210> SEQ ID NO 13
<211> LENGTH: 484
<212> TYPE: PRT
<213> ORGANISM: Xyllela fastidiosa
<220> FEATURE:

<400> SEQUENCE: 13

Met Leu Leu Ala Asp Leu Asn Ser Val Thr Asp Ile Ala Ser Ser Pro
1               5                   10                  15

Arg Leu Leu Ser Lys Tyr Ser Ala Ala Ala Asp Leu Ile Leu Arg Val
            20                  25                  30

Phe Asp Leu Thr Met Val Val Leu Ser Gly Val Met Ile Tyr Arg Leu
        35                  40                  45

Leu Phe Gly Thr Trp Met Leu Met Val Pro Tyr Arg Ile Ala Ile Gly
    50                  55                  60

Asn Thr Leu Leu Tyr Ser Val Ile Cys Phe Ser Phe Phe Pro Leu Tyr
65                  70                  75                  80

Arg Ser Trp Arg Gly Arg Ala Leu Ala Arg Glu Leu Leu Val Leu Ser
                85                  90                  95

Ser Ala Phe Cys Gly Val Phe Ile Leu Phe Ser Leu His Thr Leu Ile
```

-continued

```
            100                 105                 110

Val Gln Leu Gly His Pro Val Ser Trp Leu Trp Ile Thr Phe Trp Phe
        115                 120                 125

Leu Gly Ala Leu Ser Thr Leu Leu Ser Ala Arg Val Ala Leu Arg Ser
    130                 135                 140

Leu Leu Asn Trp Leu His Met Arg Gly Val Asp Val Gln Arg Ile Val
145                 150                 155                 160

Val Val Gly Leu Arg His Pro Val Met Lys Ile His His Tyr Leu Asn
                165                 170                 175

Arg Asn Thr Trp Thr Gly Met Gln Leu Ile Gly Tyr Phe Ser Thr Ser
            180                 185                 190

Tyr Asp Val Ser Val Ser Glu Tyr Val Arg Arg Leu Pro Ser Leu Gly
        195                 200                 205

Thr Pro Asp Arg Leu Phe Asp Phe Leu Glu Lys Asn His Val Glu Gln
    210                 215                 220

Val Trp Ile Ser Met Pro Leu Gly Glu Arg Asp Tyr Ile Lys Thr Leu
225                 230                 235                 240

Leu Lys Lys Leu Glu Arg Tyr Pro Ile Asn Val Lys Leu Ile Pro Asp
                245                 250                 255

Leu Phe Asp Phe Gly Thr Leu Asn Gln Ser Gly Glu Gln Ile Gly His
            260                 265                 270

Val Pro Val Ile Asn Leu Arg Gln Gly Gly Val Asp Arg Asp Asn Tyr
        275                 280                 285

Phe Phe Val Ala Lys Thr Ile Gln Asp Lys Val Leu Ala Met Ile Ala
    290                 295                 300

Leu Leu Leu Leu Trp Pro Leu Leu Ile Ile Ile Gly Ile Gly Ile Lys
305                 310                 315                 320

Phe Ser Ser Pro Gly Pro Val Leu Phe Arg Gln Arg Arg His Gly Leu
                325                 330                 335

Asn Gly Arg Glu Phe Tyr Val Leu Lys Phe Arg Ser Met Arg Val His
            340                 345                 350

Asp Asp Gln Ser Gln His Leu Lys Gln Ala Ser Arg Asn Asp Ser Arg
        355                 360                 365

Ile Thr Ala Phe Gly Ala Phe Leu Arg Arg Thr Ser Leu Asp Glu Leu
    370                 375                 380

Pro Gln Ile Phe Asn Val Leu Gly Gly Ser Met Ser Ile Val Gly Pro
385                 390                 395                 400

Arg Pro His Ala Ala Gln His Asn Ser Tyr Tyr Glu Lys Leu Ile Gln
                405                 410                 415

His Tyr Met Gln Arg His Tyr Val Lys Pro Gly Ile Thr Gly Trp Ala
            420                 425                 430

Gln Val Asn Gly Phe Arg Gly Glu Thr Gln Glu Leu Arg Thr Met Lys
        435                 440                 445

Lys Arg Ile Gln Tyr Asp Leu Asp Tyr Ile Arg Arg Trp Ser Leu Trp
    450                 455                 460

Phe Asp Phe Arg Ile Ile Val Leu Thr Leu Val Arg Val Leu Gly Gln
465                 470                 475                 480

Lys Asn Ala Tyr


<210> SEQ ID NO 14
<211> LENGTH: 424
<212> TYPE: PRT
<213> ORGANISM: Xyllela fastidiosa
<220> FEATURE:
```

-continued

<400> SEQUENCE: 14

```
Met Leu Met Arg Met Arg Lys Ile Thr Lys Glu His Ser Arg Asn Leu
1               5                   10                  15

Leu Val Gly Ile Val Leu Phe Phe Gly Val Ala Tyr Asn Phe Pro Leu
            20                  25                  30

Ala Met Ile Asn Ala Lys Val Phe Thr Val Thr Pro Val Met Thr Tyr
        35                  40                  45

Ala Val Glu Leu Val Ile Tyr Phe Ala Cys Phe Ile Leu Gly Leu Ser
    50                  55                  60

Ala Leu Asp Arg Lys Arg Val Val Leu Val Met Ser Gly Leu Gly Phe
65                  70                  75                  80

Leu Val Ala Leu Thr Leu Leu Arg Phe Leu Met Ser Leu Asp Phe Asp
                85                  90                  95

Pro Lys Phe Phe Arg Asp Ala Leu Ile Pro Phe Ala Phe Leu Ile Leu
            100                 105                 110

Gly Ala Ala Tyr Arg Gly Ser Leu Leu Arg Leu Phe Met Gly Met Ser
        115                 120                 125

Ile Phe Ile Thr Phe Val Ala Val Phe Glu Leu Met Met Pro Asp Val
    130                 135                 140

Tyr Gly Asp Ile Ala Asn Pro Lys Ser Tyr Phe Val Asn Ser Arg Gly
145                 150                 155                 160

Ala Ser Ala Asp Gly Phe Trp Asn Glu Gly Ser Ser Leu Tyr Leu Ser
                165                 170                 175

Ala Thr Arg Pro Asp Glu Arg Asn Phe Phe Ala Gly Ser Asn Leu Pro
            180                 185                 190

Arg Ala Ser Ser Val Phe Ile Glu Pro Val Thr Met Gly Asn Tyr Ile
        195                 200                 205

Ile Phe Phe Ala Ala Ile Val Leu Val Phe Trp Arg Trp Met Ser Val
    210                 215                 220

Ser Glu Leu Ile Leu Ser Ile Ala Met Ile Leu Phe Leu Ile Val Ala
225                 230                 235                 240

Ser Asp Gly Arg Leu Ala Thr Gly Thr Cys Ile Leu Met Val Leu Leu
                245                 250                 255

Ala Pro Phe Leu Lys Arg Phe Asp Gln Arg Phe Ala Phe Leu Leu Phe
            260                 265                 270

Phe Ser Val Leu Leu Gly Gly Trp Phe Ile Val Gln Val Asn Gly Ile
        275                 280                 285

His Ala Tyr Asp Lys Asp Thr Ile Leu Ser Arg Thr Phe Phe Ser Val
    290                 295                 300

Tyr Ser Leu Ala His Leu Pro Leu Asp Ser Trp Phe Gly Leu Asp Val
305                 310                 315                 320

Gln Ser Ser Tyr Arg Tyr Phe Asp Ser Gly Ile Ala Tyr Phe Ile Ala
                325                 330                 335

Ser Gln Ser Val Ile Thr Val Leu Val Phe Leu Leu Ala Tyr Ser Phe
            340                 345                 350

Leu Phe Asp Met Gln Ser His Glu Gly Arg Gly Phe Lys Asn Met Ala
        355                 360                 365

Ile Phe Ala Phe Ala Leu Ser Leu Leu Val Ser Asn Ser Tyr Phe Ser
    370                 375                 380

Ile Lys Thr Ser Ala Leu Trp Trp Phe Thr Cys Gly Cys Leu Trp Asn
385                 390                 395                 400

Cys Ser Pro Lys Val Leu Ala Ala Lys Lys Asn Leu Val Glu Ala Arg
```

-continued

```
            405                 410                 415

Val Ile Ala Gln Gly Gly Val Ser
            420


<210> SEQ ID NO 15
<211> LENGTH: 363
<212> TYPE: PRT
<213> ORGANISM: Xyllela fastidiosa
<220> FEATURE:

<400> SEQUENCE: 15

Met Ile His Glu Lys Lys Tyr Val Pro Val Arg Gly Gly Thr Leu Ala
1               5                   10                  15

His Ser Pro Gly Ser Leu Ser Val Gly Arg Asp Ala Arg Ile Asp Ala
            20                  25                  30

Ala Lys Gly Leu Gly Ile Phe Leu Val Val Leu Gly His Ala Lys Gly
        35                  40                  45

Leu Pro Glu Trp Trp Val Val Leu Ile Tyr Ser Phe His Val Pro Leu
    50                  55                  60

Phe Phe Leu Leu Ser Gly Trp Ala Ala Gly Thr Asn Met Arg Gln Ser
65                  70                  75                  80

Gly Phe Cys Glu Cys Leu Leu His Leu Met Arg Thr Leu Leu Val Pro
                85                  90                  95

Tyr Val Phe Phe Phe Phe Val Gly Tyr Ile Tyr Trp Leu Leu Thr Arg
            100                 105                 110

His Ile Gly Ala Lys Asp Leu Arg Trp Gly Met His Pro Trp Trp Glu
        115                 120                 125

Pro Leu Asn Gly Leu Leu Met Gly Gly Gly Thr Ala Leu Tyr Val His
    130                 135                 140

Pro Ser Leu Trp Phe Leu Pro Ala Leu Phe Val Thr Lys Leu Thr Tyr
145                 150                 155                 160

Gln Met Leu Ser Lys Tyr Val Ser Leu Glu Arg Leu Val Leu Phe Gly
                165                 170                 175

Gly Ile Phe Ser Trp Val Trp Val Gly Phe Phe Pro Gly Phe Gly Val
            180                 185                 190

Arg Phe Pro Phe Ala Leu Asp Glu Leu Pro Ile Ala Phe Leu Phe Phe
        195                 200                 205

Val Phe Gly Val Met Gly Arg Arg Thr Ser Trp Leu Arg Leu Leu Pro
    210                 215                 220

Lys Thr Arg Lys Ala Asn Met Ile Leu Leu Ala Val Leu Leu Phe Pro
225                 230                 235                 240

Trp Phe Leu Leu Ala Leu Cys Asn Glu Lys Val Asp Met Asn Met Leu
                245                 250                 255

Ile Phe Gly Asn Ser Pro Phe Val Phe His Val Ser Ala Leu Leu Gly
            260                 265                 270

Val Ala Ile Val Leu Cys Ala Ala Ala Leu Val Glu Gln Trp Ser Leu
        275                 280                 285

Val Gln Trp Ala Gly Arg Asn Thr Leu Leu Ile Leu Cys Thr His Thr
    290                 295                 300

Leu Val Phe Phe Val Leu Phe Gly Val Leu Ser Leu Leu Gly Gly Thr
305                 310                 315                 320

Ser Gly Leu Ile Leu Ala Leu Leu Phe Ser Ala Ile Thr Leu Cys Phe
                325                 330                 335

Ile Pro Ile Phe Arg Trp Ile Leu Met Arg Trp Ile Pro Trp Ser Leu
            340                 345                 350
```

-continued

```
Gly Ala Cys Ser Tyr Met Arg Ser Arg Ser Ser
        355                 360


<210> SEQ ID NO 16
<211> LENGTH: 380
<212> TYPE: PRT
<213> ORGANISM: Xyllela fastidiosa
<220> FEATURE:

<400> SEQUENCE: 16

Met Lys Val Val His Val Val Arg Gln Phe His Pro Ser Ile Gly Gly
1               5                   10                  15

Met Glu Asp Val Val Phe Asn Ile Ala Met Gln Leu His Leu His Ala
            20                  25                  30

Gly Ile Asp Val Asp Val Val Thr Leu Asn Arg Val Phe Thr Gln Ser
        35                  40                  45

Asp Val Leu Leu Pro Cys Thr Asp Lys Tyr Gln Gly Val Ser Ile Gln
    50                  55                  60

Arg Ile Gly Tyr Arg Gly Ser Ser Arg Tyr Pro Leu Ala Pro Trp Val
65                  70                  75                  80

Leu Arg Met Leu Asp Lys Ala Asp Val Ile His Val His Gly Ile Asp
                85                  90                  95

Phe Phe Tyr Asp Phe Leu Ala Leu Thr Arg Val Leu His Gly Lys Pro
            100                 105                 110

Met Val Val Ser Thr His Gly Gly Phe Phe His Thr Asp Tyr Ala Ser
        115                 120                 125

Arg Leu Lys Leu Leu Trp Phe Asn Thr Leu Thr Arg Leu Ser Ala Leu
    130                 135                 140

Ala Tyr Ala Arg Ile Ile Ala Ser Ser Glu Ser Asp Gly Ala Leu Phe
145                 150                 155                 160

Ser Lys Ile Val Ala Pro Ser Arg Leu Arg Val Ile Glu Asn Gly Val
                165                 170                 175

Asp Val Glu Lys Tyr Ala Arg Cys Gly Ala Ser Glu Ala Gly Arg Thr
            180                 185                 190

Leu Leu Tyr Phe Gly Arg Trp Ser Met Asn Lys Gly Leu Leu Glu Thr
        195                 200                 205

Leu Gln Leu Leu Ala Val Leu Tyr Val Leu Asp Pro Arg Trp Arg Leu
    210                 215                 220

Ile Ile Ala Gly Arg Glu Tyr Asp Tyr Asp Gln Ala Ala Leu Ala Tyr
225                 230                 235                 240

Glu Val Asp Arg Leu Gly Leu Ser Glu Gln Val His Phe His Cys Ser
                245                 250                 255

Pro Ser Gln Ser Gln Leu Arg Phe Leu Met Glu Gln Ala Gln Phe Phe
            260                 265                 270

Ile Ser Leu Ser Arg His Glu Gly Phe Gly Ile Ala Ala Val Glu Ala
        275                 280                 285

Met Ser Ala Gly Leu Ile Pro Val Leu Ser Asp Ile Pro Pro Phe Ala
    290                 295                 300

Arg Leu His Arg Glu Ser Gly Leu Gly Val Leu Val Asp Pro Leu Gln
305                 310                 315                 320

Pro Gln Gln Ala Ala Val Ala Val Gln Gly Leu Ala Val Gln Val Asp
                325                 330                 335

Thr His Phe Ile Asp Trp Arg Ser Gln Ala Met Ala Phe Ser Asp Arg
            340                 345                 350
```

-continued

```
Tyr His Trp Arg Tyr Val Ile Gly Cys Tyr Gln Asp Glu Tyr Cys Arg
        355                 360                 365

Ala Leu Gly Leu Gly Gly Glu Gln Glu Phe Leu Arg
    370                 375                 380


<210> SEQ ID NO 17
<211> LENGTH: 510
<212> TYPE: PRT
<213> ORGANISM: Xyllela fastidiosa
<220> FEATURE:

<400> SEQUENCE: 17

Met Ser Asp Ser Val Val Ser Val Ser Ala Val Ser Glu Arg Ser Leu
1               5                   10                  15

Ala Ser Arg Ala Leu Gly Gly Ala Val Val Thr Met Leu Gly Gln Gly
            20                  25                  30

Ala Arg Val Val Ile Gln Phe Ser Ile Ile Val Leu Leu Ala Arg Leu
        35                  40                  45

Leu Asn Pro His Asp Tyr Gly Leu Met Ala Met Val Thr Ala Ile Val
    50                  55                  60

Gly Val Ala Asp Ile Leu Arg Asp Phe Gly Leu Ser Ser Ala Ala Ile
65                  70                  75                  80

Gln Ala Lys Gln Ile Thr Asn Ala Gln Arg Asp Asn Leu Phe Trp Ile
                85                  90                  95

Asn Ser Val Ile Gly Leu Ala Leu Ser Leu Val Val Phe Val Ala Ala
            100                 105                 110

Gln Leu Ile Ala Asp Phe Tyr Arg Glu Pro Ala Leu Val Thr Ile Thr
        115                 120                 125

Gln Val Leu Ala Ile Asn Phe Leu Leu Asn Gly Met Ala Thr Gln Tyr
    130                 135                 140

Arg Ala Asn Leu Ser Arg Glu Met Arg Phe Gly Gln Leu Ala Leu Ser
145                 150                 155                 160

Asp Ile Gly Ala Gln Val Leu Gly Leu Leu Val Gly Val Ser Val Ala
                165                 170                 175

Leu Val Gly Trp Gly Val Trp Ala Leu Val Leu Gln Gln Val Val Gln
            180                 185                 190

Ala Val Ala Asn Leu Val Ile Ala Met Val Cys Ala Arg Trp Leu Pro
        195                 200                 205

Gly Gly Tyr Arg Arg Gly Val Pro Met Gly Ser Phe Leu Ser Phe Gly
    210                 215                 220

Trp Asn Leu Met Val Ala Gln Leu Leu Ser Tyr Ala Asn Arg Ser Val
225                 230                 235                 240

Gly Gln Val Ile Ile Gly Tyr Arg Leu Gly Pro Asn Val Leu Gly Leu
                245                 250                 255

Tyr Asn Arg Ala Phe Gln Leu Leu Met Met Pro Leu Asn Gln Val Ile
            260                 265                 270

Ala Pro Ala Ser Ser Val Ala Leu Pro Val Leu Ser Gln Leu Gln Asp
        275                 280                 285

Asp Arg Ala Arg Phe Asp Ser Phe Leu Leu Arg Gly Gln Thr Met Met
    290                 295                 300

Leu His Val Ile Val Ala Leu Phe Ala Phe Ser Cys Ala Gln Ala Thr
305                 310                 315                 320

Pro Leu Ile Val Leu Val Leu Gly Glu Lys Trp Arg Ser Ala Val Leu
                325                 330                 335

Leu Phe Gln Ile Leu Thr Leu Ala Gly Met Thr Gln Ser Ala Ser Tyr
```

-continued

```
            340                 345                 350

Ala Ser Tyr Trp Leu Phe Leu Ala Arg Gly Leu Ile Arg Asp His Leu
        355                 360                 365

Leu Phe Ser Ile Val Ser His Val Phe Leu Val Leu Cys Val Cys Ile
    370                 375                 380

Gly Ala Tyr Trp Gly Val Phe Gly Val Ala Ile Gly Tyr Ser Ile Ser
385                 390                 395                 400

Leu Ala Leu Ile Trp Pro Leu Ser Ile Ile Trp Ala Ala Arg Ile Thr
                405                 410                 415

Pro Val Pro Gly Trp Glu Met Phe Phe Asn Gly Met Arg Ala Ile Val
            420                 425                 430

Gly Tyr Gly Val Cys Ala Phe Ala Ser Met Tyr Ala Ser Gln Trp Cys
        435                 440                 445

Asp Glu Ser Asn Leu Trp Lys Gln Leu Ile Val Gly Ala Leu Ala Met
    450                 455                 460

Leu Val Ala Phe Ala Val Leu Ser Leu Leu Trp Ser Ala Phe Arg Arg
465                 470                 475                 480

Asp Val Leu Ser Ile Ile Lys Ile Gly Met Ser Ser Ser Val Val Ser
                485                 490                 495

Ser Phe Leu Leu Arg Ile Met Arg Arg Val Arg Lys Gly Ser
            500                 505                 510


<210> SEQ ID NO 18
<211> LENGTH: 281
<212> TYPE: PRT
<213> ORGANISM: Xyllela fastidiosa
<220> FEATURE:

<400> SEQUENCE: 18

Met Leu Phe Arg Trp Tyr Val Gln His Pro Pro Glu Ile Leu Leu Gln
1               5                   10                  15

Trp Ile Arg Glu Ala Asp Ile Ile Leu Phe Glu Ser Gly Thr Ala Val
            20                  25                  30

Ala Phe Ile Asp Met Ala Lys Arg Ile Asn Pro Ser Ala Arg Leu Ile
        35                  40                  45

Tyr Asn Ala Ser Asp Ser Leu Ser Ala Ile Asn Val Ala Cys Tyr Ile
    50                  55                  60

Glu Arg Glu Phe Gln Arg Val Ala Ala Ser Leu Asp Val Ile Ala Val
65                  70                  75                  80

Val Ser Pro Ala Met Thr Lys Glu Ile Pro Ser His Gly Asn Val Phe
                85                  90                  95

Tyr Ile Gly His Gly Val Leu Gln Asn Leu Ser Glu Leu Gly Gly Pro
            100                 105                 110

Ser Pro Tyr Glu Gly Gly Ile His Ala Val Ser Val Gly Ser Met Leu
        115                 120                 125

Phe Asp Pro Leu Phe Phe Val Val Ala Gly Lys Glu Phe Pro His Ile
    130                 135                 140

Thr Phe His Val Ile Gly Ser Gly Met Gly Arg His Pro Asp Tyr Pro
145                 150                 155                 160

Asp Asn Val Val Val Tyr Gly Glu Met Lys Tyr Val Glu Thr Ile Arg
                165                 170                 175

Tyr Ile Arg His Ala Ser Phe Gly Ile Ala Pro Tyr Val Ser Gln Gln
            180                 185                 190

Val Pro Glu Tyr Leu Ala Asp Ser Ser Met Lys Leu Leu Gln Tyr Asp
        195                 200                 205
```

-continued

```
Phe Phe Gly Leu Pro Ala Val Cys Pro His Ala Val Val Gly Ser Tyr
    210                 215                 220

Pro Thr Arg Phe Gly Tyr Thr Pro Gly Asn Ala Ile Glu Leu Val Ala
225                 230                 235                 240

Ala Ile Lys Arg Ala Leu Gln Ala Pro His Gln Gln Ser Arg Gln Tyr
                245                 250                 255

Leu Ser Trp Glu Glu Val Val Ala Arg Val Leu Asp Pro Thr Ala Tyr
            260                 265                 270

Glu Gly Thr Arg Ile Leu Pro Ala Val
        275                 280


<210> SEQ ID NO 19
<211> LENGTH: 264
<212> TYPE: PRT
<213> ORGANISM: Xyllela fastidiosa
<220> FEATURE:

<400> SEQUENCE: 19

Met Trp Ala Phe Gly Asp Phe Val Val Thr Ile Ser Gly Ile Ser Ser
1               5                   10                  15

Asp Pro Pro Phe Ile Glu Thr Ile Asp Thr Leu Leu Leu Gly Gly Phe
            20                  25                  30

Pro Val Leu Ser Thr Thr Pro Ser Ala Phe Val Ala Ser Leu Tyr Arg
        35                  40                  45

Ser Leu Thr Glu Glu Arg Pro Gln Arg Val Phe Phe Ala Asn Thr Asn
    50                  55                  60

Phe Ile Val Gln Cys Gln Ser Leu Arg Gly Arg Met Tyr Ser Glu Arg
65                  70                  75                  80

Val Cys Ile Leu Asn Asp Gly Ile Gly Met Asp Leu Ala Ala Leu Phe
                85                  90                  95

Ile His Gly Arg Arg Phe Val Ser Asn Leu Asn Gly Thr Asp Leu Ile
            100                 105                 110

Pro Tyr Leu Cys Gln His Ala Pro Arg Pro Leu Arg Phe Phe Leu Leu
        115                 120                 125

Gly Ala Lys Pro Gly Val Ala Asp Met Ala Ala Gln Thr Leu Cys Gln
    130                 135                 140

Leu Gly Gln Leu Val Val Gly Thr Cys Asp Gly Tyr Ala Gln Phe Ile
145                 150                 155                 160

Ala Ala Gly Glu Asp Leu Val Glu Ser Ile Asn Ala Ser Gly Ala Asp
                165                 170                 175

Val Leu Leu Val Ala Leu Gly Asn Pro Val Gln Glu Arg Trp Ile Leu
            180                 185                 190

Asp His Asp Val Gln Leu His Thr Pro Leu Val Phe Gly Val Gly Ala
        195                 200                 205

Leu Phe Asp Phe Met Ser Gly Asn Val Arg Arg Ala Pro Leu Trp Val
    210                 215                 220

Arg Arg Val Arg Gly Glu Trp Leu Tyr Arg Leu Leu Leu Glu Pro Arg
225                 230                 235                 240

Arg Leu Phe Lys Arg Tyr Ser Trp Asp Leu Arg Phe Phe Gly Val Cys
                245                 250                 255

Leu Leu Arg Arg Arg Gly Val Asn
            260


<210> SEQ ID NO 20
<211> LENGTH: 213
```

-continued

<212> TYPE: PRT
<213> ORGANISM: Xanthomonas compestris

<400> SEQUENCE: 20

```
Met Ser Leu Gly Ala Cys Ser Thr Gly Pro Glu Met Ala Ser Ser Leu
1               5                   10                  15

Pro His Pro Asp Pro Leu Ala Met Ser Thr Val Gln Pro Glu Tyr Arg
            20                  25                  30

Leu Ala Pro Gly Asp Leu Leu Leu Val Lys Val Phe Gln Ile Asp Asp
        35                  40                   45

Leu Glu Arg Gln Val Arg Ile Asp Gln Asn Gly His Ile Ser Leu Pro
    50                  55                  60

Leu Ile Gly Asp Val Lys Ala Ala Gly Leu Gly Val Gly Glu Leu Glu
65                  70                  75                  80

Lys Leu Val Ala Asp Arg Tyr Arg Ala Gly Tyr Leu Gln Gln Pro Gln
                85                  90                  95

Ile Ser Val Phe Val Gln Glu Ser Asn Gly Arg Arg Val Thr Val Thr
            100                 105                 110

Gly Ala Val Asp Glu Pro Gly Ile Tyr Pro Val Ile Gly Ala Asn Leu
        115                 120                 125

Thr Leu Gln Gln Ala Ile Ala Gln Ala Lys Gly Val Ser Thr Val Ala
    130                 135                 140

Ser Arg Gly Asn Val Ile Val Phe Arg Met Val Asn Gly Gln Lys Met
145                 150                 155                 160

Ile Ala Arg Phe Asp Leu Thr Glu Ile Glu Lys Gly Ala Asn Pro Asp
                165                 170                 175

Pro Glu Ile Tyr Gly Gly Asp Ile Val Val Val Tyr Arg Ser Asp Ala
            180                 185                 190

Arg Val Trp Leu Arg Thr Met Leu Glu Leu Thr Pro Leu Val Met Val
        195                 200                 205

Trp Arg Ala Tyr Arg
    210
```

<210> SEQ ID NO 21
<211> LENGTH: 449
<212> TYPE: PRT
<213> ORGANISM: Xanthomonas compestris

<400> SEQUENCE: 21

```
Met Asp Tyr Trp Arg Ala Leu Val Ser Gln Leu Trp Leu Ile Ile Leu
1               5                   10                  15

Ile Ala Val Gly Ala Leu Leu Leu Ala Phe Gly Ile Thr Met Leu Met
            20                  25                  30

Pro Glu Lys Tyr Arg Ala Thr Ser Thr Leu Gln Ile Glu Arg Asp Ser
        35                  40                  45

Leu Asn Val Val Asn Val Asp Asn Leu Met Pro Val Glu Ser Pro Gln
    50                  55                  60

Asp Arg Asp Phe Tyr Gln Thr Gln Tyr Gln Leu Leu Gln Ser Arg Ser
65                  70                  75                  80

Leu Ala Arg Ala Val Ile Arg Glu Ala Lys Leu Asp Gln Glu Pro Ala
                85                  90                  95

Phe Lys Glu Gln Val Glu Glu Ala Leu Ala Lys Ala Ala Glu Lys Asn
            100                 105                 110

Pro Glu Ala Gly Lys Ser Leu Asp Ser Arg Gln Ala Ile Val Glu Arg
        115                 120                 125
```

-continued

```
Ser Leu Thr Asp Thr Leu Leu Ala Gly Leu Val Val Glu Pro Ile Leu
    130                 135                 140

Asn Ser Arg Leu Val Tyr Val Asn Tyr Asp Ser Pro Asp Pro Val Leu
145                 150                 155                 160

Ala Ala Lys Ile Ala Asn Thr Tyr Pro Lys Val Phe Ile Val Ser Thr
                165                 170                 175

Gln Glu Arg Arg Met Lys Ala Ser Ser Phe Ala Thr Gln Phe Leu Ala
            180                 185                 190

Glu Arg Leu Lys Gln Leu Arg Glu Lys Val Glu Asp Ser Glu Lys Asp
        195                 200                 205

Leu Val Ser Tyr Ser Thr Glu Glu Gln Ile Val Ser Val Gly Asp Asp
    210                 215                 220

Lys Pro Ser Leu Pro Ala Gln Asn Leu Thr Asp Leu Asn Ala Leu Leu
225                 230                 235                 240

Ala Ser Ala Gln Asp Ala Arg Ile Lys Ala Glu Ser Ala Trp Arg Gln
                245                 250                 255

Ala Ser Ser Gly Asp Gly Met Ser Leu Pro Gln Val Leu Ser Ser Pro
            260                 265                 270

Leu Ile Gln Ser Leu Arg Ser Glu Gln Val Arg Leu Thr Ser Glu Tyr
        275                 280                 285

Gln Gln Lys Leu Ser Thr Phe Lys Pro Asp Tyr Pro Glu Met Gln Arg
    290                 295                 300

Leu Lys Ala Gln Ile Glu Glu Ser Arg Arg Gln Ile Asn Gly Glu Val
305                 310                 315                 320

Ile Asn Ile Arg Gln Ser Leu Lys Ala Thr Tyr Asp Ala Ser Val His
                325                 330                 335

Gln Glu Gln Leu Leu Asn Asp Arg Ile Ala Gly Leu Arg Ser Asn Glu
            340                 345                 350

Leu Asp Leu Gln Ser Arg Ser Ile Arg Tyr Asn Met Leu Lys Arg Asp
        355                 360                 365

Val Asp Thr Asn Arg Gln Leu Tyr Asp Ala Leu Leu Gln Arg Tyr Lys
    370                 375                 380

Glu Ile Gly Val Ala Ser Asn Val Gly Ala Asn Asn Val Thr Ile Val
385                 390                 395                 400

Asp Thr Ala Asp Val Pro Thr Ser Lys Thr Ser Pro Lys Leu Lys Leu
                405                 410                 415

Asn Leu Ala Leu Gly Leu Ile Phe Gly Val Phe Leu Gly Val Ala Val
            420                 425                 430

Ala Leu Val Arg Tyr Phe Leu Arg Gly Pro Ser Pro Arg Ser Arg Leu
        435                 440                 445

Asn
```

<210> SEQ ID NO 22
<211> LENGTH: 484
<212> TYPE: PRT
<213> ORGANISM: Xanthomonas compestris

<400> SEQUENCE: 22

```
Met Leu Leu Ala Asp Leu Ser Ser Ala Thr Tyr Thr Thr Ser Ser Pro
1               5                   10                  15

Arg Leu Leu Ser Lys Tyr Ser Ala Ala Ala Asp Leu Val Leu Arg Val
            20                  25                  30

Phe Asp Leu Thr Met Val Val Ala Ser Gly Leu Ile Ala Tyr Arg Ile
        35                  40                  45
```

-continued

Val Phe Gly Thr Trp Val Pro Ala Ala Pro Tyr Arg Val Ala Ile Ala
50 55 60

Thr Thr Leu Leu Tyr Ser Val Ile Cys Phe Ala Leu Phe Pro Leu Tyr
65 70 75 80

Arg Ser Trp Arg Gly Arg Gly Leu Leu Ser Glu Leu Val Val Leu Gly
85 90 95

Gly Ala Phe Gly Gly Val Phe Ala Leu Phe Ala Val His Ala Leu Ile
100 105 110

Val Gln Val Gly Glu Gln Val Ser Arg Gly Trp Val Gly Leu Trp Phe
115 120 125

Val Gly Gly Leu Val Ser Leu Val Ala Ala Arg Thr Leu Leu Arg Gly
130 135 140

Phe Leu Asn His Leu Arg Thr Gln Gly Val Asp Val Gln Arg Val Val
145 150 155 160

Val Val Gly Leu Arg His Pro Val Met Lys Ile Ser His Tyr Leu Ser
165 170 175

Arg Asn Pro Trp Val Gly Met Asn Met Val Gly Tyr Phe Arg Thr Pro
180 185 190

Tyr Asp Leu Ala Val Ala Glu Gln Arg Gln Gly Leu Pro Cys Leu Gly
195 200 205

Asp Pro Asp Glu Leu Ile Glu Tyr Leu Lys Asn Asn Gln Val Glu Gln
210 215 220

Val Trp Ile Ser Leu Pro Leu Gly Glu Arg Asp His Ile Lys Gln Leu
225 230 235 240

Leu Gln Arg Leu Asp Arg Tyr Pro Ile Asn Val Lys Leu Val Pro Asp
245 250 255

Leu Phe Asp Phe Gly Leu Leu Asn Gln Ser Ala Glu Gln Ile Gly Ser
260 265 270

Val Pro Val Ile Asn Leu Arg Gln Gly Gly Val Asp Arg Asp Asn Tyr
275 280 285

Phe Val Val Ala Lys Ala Leu Gln Asp Lys Ile Leu Ala Val Ile Ala
290 295 300

Leu Met Gly Leu Trp Pro Leu Met Leu Ala Ile Ala Val Gly Val Lys
305 310 315 320

Met Ser Ser Pro Gly Pro Val Phe Phe Arg Gln Arg Arg His Gly Leu
325 330 335

Gly Gly Arg Glu Phe Tyr Met Phe Lys Phe Arg Ser Met Arg Val His
340 345 350

Asp Asp His Gly Thr Thr Ile Gln Gln Ala Thr Lys Asn Asp Thr Arg
355 360 365

Ile Thr Arg Phe Gly Ser Phe Leu Arg Arg Ser Ser Leu Asp Glu Leu
370 375 380

Pro Gln Ile Phe Asn Val Leu Gly Gly Ser Met Ser Ile Val Gly Pro
385 390 395 400

Arg Pro His Ala Ala Gln His Asn Thr His Tyr Glu Lys Leu Ile Asn
405 410 415

His Tyr Met Gln Arg His Tyr Val Lys Pro Gly Ile Thr Gly Trp Ala
420 425 430

Gln Val Asn Gly Phe Arg Gly Glu Thr Pro Glu Leu Arg Thr Met Lys
435 440 445

Lys Arg Ile Gln Tyr Asp Leu Asp Tyr Ile Arg Arg Trp Ser Leu Trp
450 455 460

Leu Asp Ile Arg Ile Ile Val Leu Thr Ala Val Arg Val Leu Gly Gln

-continued

```
465                 470                 475                 480

Lys Thr Ala Tyr


<210> SEQ ID NO 23
<211> LENGTH: 432
<212> TYPE: PRT
<213> ORGANISM: Xanthomonas compestris

<400> SEQUENCE: 23

Met Leu Ile Gln Met Ser Glu Gln Ala Arg Val Arg Trp His Asn Ala
1               5                   10                  15

Leu Ile Glu Leu Thr Leu Leu Thr Gly Val Gly Tyr Asn Leu Leu Leu
            20                  25                  30

Ala Leu Ile Asn Ala Asn Val Phe Thr Val Arg Pro Val Ile Thr Tyr
        35                  40                  45

Ala Val Glu Phe Leu Val Tyr Ala Ala Cys Phe Leu Leu Gly Leu Gly
    50                  55                  60

Ser Met Ser Arg Gln Arg Ile Ala Met Ile Phe Gly Gly Leu Gly Leu
65                  70                  75                  80

Ile Val Thr Leu Met Phe Val Arg Phe Leu Val Asn Trp Gln Ile Asp
                85                  90                  95

Pro Lys Phe Phe Arg Asp Ala Leu Val Val Phe Ala Phe Val Val Leu
            100                 105                 110

Gly Ser Ala Tyr Thr Gly Ser Leu Pro Lys Leu Phe Ile Arg Met Thr
        115                 120                 125

Ile Ile Val Ser Leu Val Ala Ala Phe Glu Leu Ala Met Pro Ser Ala
    130                 135                 140

Tyr Gly Asp Leu Val Asn Pro Lys Ser Phe Phe Val Asn Ala Arg Gly
145                 150                 155                 160

Met Ser Ala Glu Gly Phe Trp Asn Glu Asp Ser Asn Leu Phe Val Ser
                165                 170                 175

Ala Thr Arg Pro Gly Glu Arg Asn Phe Leu Pro Gly Ser Asn Leu Pro
            180                 185                 190

Arg Ala Ser Ser Trp Phe Ile Glu Pro Val Thr Met Gly Asn Tyr Ile
        195                 200                 205

Cys Phe Phe Thr Ala Ile Val Leu Thr Phe Trp Arg Trp Met Arg Pro
    210                 215                 220

Ser Met Leu Ile Leu Ser Ile Gly Leu Ile Gly Phe Met Ile Val Ala
225                 230                 235                 240

Ser Asp Gly Arg Leu Ala Ala Gly Thr Cys Val Leu Met Val Leu Leu
                245                 250                 255

Ser Pro Leu Leu Lys Arg Met Asp Gln Arg Leu Ala Phe Leu Leu Phe
            260                 265                 270

Leu Phe Val Ile Ala Ser Ala Trp Leu Leu Val Trp Met Thr Gly Ile
        275                 280                 285

Thr Ala Tyr Gln Asp Thr Thr Met Gly Arg Ile Phe Phe Thr Val Asn
    290                 295                 300

Ser Met Asn Asn Leu Ser Phe Glu Ser Trp Met Gly Leu Asp Phe Ala
305                 310                 315                 320

Gln Ala Tyr Arg Tyr Phe Asp Ser Gly Ile Ser Tyr Phe Ile Ala Ser
                325                 330                 335

Gln Ser Ile Val Gly Val Leu Ala Phe Leu Leu Ser Tyr Ser Phe Leu
            340                 345                 350

Leu Leu Met Pro Ser Lys Glu Gly Gln Leu Phe Lys Asn Gln Ala Met
```

-continued

```
        355                 360                 365

Phe Ala Phe Ala Leu Ser Leu Leu Val Ser Asn Gly Tyr Phe Ser Ile
    370                 375                 380

Lys Thr Ser Ala Leu Trp Trp Phe Val Cys Gly Cys Met Trp His Leu
385                 390                 395                 400

Met Pro Ala Ala Ser Ala Val Pro Val Arg Asp Glu Ser Lys Glu Asp
                405                 410                 415

Pro Thr Asp Asn Gly Val His Val Pro Leu Pro Ala Gly Ala Pro Arg
            420                 425                 430


<210> SEQ ID NO 24
<211> LENGTH: 364
<212> TYPE: PRT
<213> ORGANISM: Xanthomonas compestris

<400> SEQUENCE: 24

Met Asn Thr Val Thr Gly Ala Ser Gly Thr Ser Ala Pro Val Gln Ala
1               5                   10                  15

Ala Gly Ala Arg Ala Phe Ala Ser Gly Arg Ser Arg Asp Pro Arg Ile
            20                  25                  30

Asp Ala Thr Lys Ala Ile Ala Ile Leu Leu Val Val Phe Cys His Ala
        35                  40                  45

Lys Gly Val Pro His Gly Met Thr Leu Phe Ala Tyr Ser Phe His Val
    50                  55                  60

Pro Leu Phe Phe Leu Val Ser Gly Trp Leu Ala Ala Gly Tyr Ala Ser
65                  70                  75                  80

Arg Thr Thr Ser Leu Leu Gln Thr Ile Thr Lys Gln Ala Arg Gly Leu
                85                  90                  95

Leu Leu Pro Tyr Val Val Phe Tyr Leu Leu Gly Tyr Val Tyr Trp Leu
            100                 105                 110

Leu Thr Arg Asn Ile Gly Glu Lys Ala Ala Arg Trp Gly Ser His Pro
        115                 120                 125

Trp Trp Glu Pro Ile Val Ser Met Phe Thr Gly Val Gly Pro Asp Leu
    130                 135                 140

Tyr Val Gln Pro Pro Leu Trp Phe Leu Pro Val Met Leu Val Thr Val
145                 150                 155                 160

Ile Gly Tyr Val Leu Leu Arg Arg Trp Met Pro Pro Leu Val Ile Ala
                165                 170                 175

Ala Val Ala Val Val Leu Ala Trp Phe Trp Met Asn Trp Phe Pro Leu
            180                 185                 190

Gln His Met Arg Leu Phe Trp Gly Leu Asp Val Leu Pro Val Ser Leu
        195                 200                 205

Cys Phe Tyr Ala Leu Gly Ala Leu Leu Ile His Val Ser Pro Tyr Leu
    210                 215                 220

Pro Thr Ser Leu Pro Gly Ser Ala Leu Val Thr Val Val Leu Ala Ala
225                 230                 235                 240

Leu Val Ala Trp Leu Ala Gly Val Asn Gly Arg Ile Asp Val Asn Met
                245                 250                 255

Leu Glu Phe Gly Arg Gln His Ala Val Phe Leu Leu Ser Ala Val Ala
            260                 265                 270

Gly Ser Leu Met Val Ile Cys Ala Ala Arg Met Val Gln Glu Trp Thr
        275                 280                 285

Trp Leu Gln Trp Ile Gly Arg Asn Thr Leu Leu Ile Leu Cys Thr His
    290                 295                 300
```

-continued

Met Leu Val Phe Phe Val Leu Ser Gly Val Ala Ala Leu Ala Gly Gly
305 310 315 320

Phe Gly Gly Ala Arg Pro Gly Leu Gly Trp Ala Ile Phe Val Thr Leu
325 330 335

Phe Ala Leu Val Ala Ser Val Pro Leu Arg Trp Phe Leu Met Arg Phe
340 345 350

Ala Pro Trp Thr Leu Gly Ala Arg Pro Val Ser Ala
355 360

<210> SEQ ID NO 25
<211> LENGTH: 380
<212> TYPE: PRT
<213> ORGANISM: Xanthomonas compestris

<400> SEQUENCE: 25

Met Lys Val Val His Val Val Arg Gln Phe His Pro Ser Ile Gly Gly
1 5 10 15

Met Glu Glu Val Val Leu Asn Val Ala Arg Gln His Gln Ala Asn Ser
20 25 30

Ala Asp Thr Val Glu Ile Val Thr Leu Asp Arg Val Phe Thr Asp Pro
35 40 45

Ser Ala Gln Leu Ala Gln His Glu Leu His Gln Gly Leu Ser Ile Thr
50 55 60

Arg Ile Gly Tyr Arg Gly Ser Ser Arg Tyr Pro Ile Ala Pro Ser Val
65 70 75 80

Leu Gly Ala Ile Arg Ser Ala Asp Val Val His Leu His Gly Ile Asp
85 90 95

Phe Phe Tyr Asp Tyr Leu Ala Leu Thr Lys Pro Leu His Gly Lys Pro
100 105 110

Met Val Val Ser Thr His Gly Gly Phe Phe His Thr Ala Tyr Ala Ser
115 120 125

Arg Met Lys Gln Ile Trp Phe Gln Thr Leu Thr Arg Thr Ser Ala Leu
130 135 140

Ala Tyr Ala Arg Val Ile Ala Thr Ser Glu Asn Asp Gly Asp Leu Phe
145 150 155 160

Ala Lys Val Val Ala Pro Ser Arg Leu Arg Val Ile Glu Asn Gly Val
165 170 175

Asp Val Glu Lys Tyr Ala Gly Gln Gly Ala Arg Ala Pro Gly Arg Thr
180 185 190

Met Leu Tyr Phe Gly Arg Trp Ser Val Asn Lys Gly Leu Ile Glu Thr
195 200 205

Leu Glu Leu Leu Gln Ala Ala Leu Thr Arg Asp Pro Gln Trp Arg Leu
210 215 220

Ile Ile Ala Gly Arg Glu Tyr Asp Leu Asn Glu Ala Asp Leu Arg Lys
225 230 235 240

Ala Ile Ala Glu Arg Gly Leu Gln Asp Lys Val Gln Leu Ser Met Ser
245 250 255

Pro Ser Gln Gln Gln Leu Cys Ala Leu Met Gln Gln Ala Gln Phe Phe
260 265 270

Val Cys Leu Ser Arg His Glu Gly Phe Gly Ile Ala Ala Val Glu Ala
275 280 285

Met Ser Ala Gly Leu Ile Pro Ile Leu Ser Asp Ile Pro Pro Phe Val
290 295 300

Arg Leu Ala Thr Glu Ser Gly Gln Gly Val Ile Val Asn Arg Asp Arg
305 310 315 320

-continued

```
Ile Gln Ala Ala Ala Asp Ser Val Gln Ala Leu Ala Leu Gln Ala Asn
                325                 330                 335

Ala Asp Phe Asp Ala Arg Arg Thr Ala Thr Met Ala Tyr Val Ala Arg
            340                 345                 350

Tyr Asp Trp Arg His Val Val Gly Arg Tyr Ile Asp Glu Tyr His Ala
        355                 360                 365

Ala Leu Gly Thr Pro Arg Thr Gln Glu Ala Val Arg
    370                 375                 380


<210> SEQ ID NO 26
<211> LENGTH: 498
<212> TYPE: PRT
<213> ORGANISM: Xanthomonas compestris

<400> SEQUENCE: 26

Met Thr Ala Glu Thr Ser Thr Met Thr Ser Pro Thr Pro Pro Pro Arg
1               5                   10                  15

Ser Leu Gly Ser Arg Ala Ala Gly Ala Ala Val Thr Met Ile Gly Gln
            20                  25                  30

Ser Ala Lys Met Ile Val Gln Phe Gly Gly Ile Val Leu Leu Ala Arg
        35                  40                  45

Leu Leu Thr Pro Tyr Asp Tyr Gly Leu Met Ala Met Val Thr Ala Ile
    50                  55                  60

Val Gly Ala Ala Glu Ile Leu Arg Asp Phe Gly Leu Ser Ala Ala Ala
65                  70                  75                  80

Val Gln Ala Lys His Val Ser Arg Glu Gln Arg Asp Asn Leu Phe Trp
                85                  90                  95

Ile Asn Ser Gly Ile Gly Leu Met Leu Ser Val Val Val Phe Ala Ser
            100                 105                 110

Ala His Trp Ile Ala Asp Phe Tyr His Glu Pro Ala Leu Val Thr Ile
        115                 120                 125

Ser Gln Ala Leu Ala Val Thr Phe Leu Leu Asn Gly Met Thr Thr Gln
    130                 135                 140

Tyr Arg Ala His Leu Ser Arg Gly Leu Arg Phe Gly Gln Val Ala Leu
145                 150                 155                 160

Ser Asp Val Gly Ser Gln Val Leu Gly Leu Gly Ala Ala Val Ala Ala
                165                 170                 175

Ala Leu Ala Gly Trp Gly Tyr Trp Ala Leu Ile Val Gln Gln Val Val
            180                 185                 190

Gln Ala Ile Val Asn Leu Ile Ile Ala Gly Ala Cys Ala Arg Trp Leu
        195                 200                 205

Pro Arg Gly Tyr Ala Arg Gln Ala Pro Met Arg Asp Phe Met Ser Phe
    210                 215                 220

Gly Trp Asn Leu Met Ala Ala Gln Leu Leu Gly Tyr Ala Ser Arg Asn
225                 230                 235                 240

Val Gly Gln Val Ile Ile Gly Trp Arg Thr Gly Pro Asp Ala Leu Gly
                245                 250                 255

Leu Tyr Asn Arg Ala Phe Gln Leu Leu Met Met Pro Leu Asn Gln Ile
            260                 265                 270

Asn Ala Pro Ala Thr Ser Val Ala Leu Pro Val Leu Ser Gln Leu Gln
        275                 280                 285

Asp Glu Arg Glu Arg Tyr Ser Ala Phe Leu Leu Arg Gly Gln Thr Val
    290                 295                 300

Met Val His Leu Ile Phe Ala Leu Phe Ala Phe Ala Cys Ala Leu Ala
```

-continued 305 310 315 320

Met Pro Leu Ile Val Leu Val Leu Gly Glu Gln Trp Arg Glu Ala Val
325 330 335

Pro Leu Phe Gln Val Leu Thr Leu Gly Gly Ile Phe Gln Thr Ala Ser
340 345 350

Tyr Ala Thr Tyr Trp Val Phe Leu Ser Lys Gly Leu Met Arg Glu Gln
355 360 365

Leu Val Tyr Ser Leu Val Gly Arg Ile Leu Leu Ile Ala Cys Ile Phe
370 375 380

Val Gly Ser Arg Trp Gly Ala Met Gly Val Ala Ile Gly Tyr Ser Phe
385 390 395 400

Gly Leu Leu Leu Ile Trp Pro Leu Ser Leu Val Trp Ile Gly Lys Ile
405 410 415

Thr Asp Ala Pro Val Gly Ala Leu Phe Val Asn Ala Met Arg Ala Leu
420 425 430

Val Ala Tyr Gly Ile Ala Gly Gly Cys Ala Tyr Tyr Ala Ser Val Thr
435 440 445

Val Gly Gly Pro Leu Trp Gln Gln Leu Leu Val Gly Ala Gly Ala Met
450 455 460

Ala Leu Val Cys Leu Leu Ala Leu Ala Trp Pro Gly Phe Arg Arg Asp
465 470 475 480

Val Val Ala Ile Val Asn Ile Arg Lys Leu Leu Thr Gln Ala Lys Ala
485 490 495

Arg Arg

<210> SEQ ID NO 27
<211> LENGTH: 295
<212> TYPE: PRT
<213> ORGANISM: Xanthomonas compestris

<400> SEQUENCE: 27

Met Phe Arg Trp Tyr Ala Ala His Pro Pro Lys Gln Leu Leu Asp Trp
1 5 10 15

Met Arg Glu Ser Asp Val Ile Val Phe Glu Ser Gly Ile Ala Val Ala
20 25 30

Phe Ile Glu Leu Ala Lys Arg Val Asn Pro Ala Ala Lys Leu Val Tyr
35 40 45

Arg Ala Ser Asp Gly Leu Ser Thr Ile Asn Val Ala Ser Tyr Ile Glu
50 55 60

Arg Glu Phe Asp Arg Val Ala Pro Thr Leu Asp Val Ile Ala Leu Val
65 70 75 80

Ser Pro Ala Met Ala Ala Glu Val Ala Ser Arg Asp Asn Val Phe His
85 90 95

Val Gly His Gly Val Asp His Asn Leu Asp Gln Leu Gly Asp Pro Ser
100 105 110

Pro Tyr Ala Glu Gly Ile His Ala Val Ala Val Gly Ser Met Leu Phe
115 120 125

Asp Pro Glu Phe Phe Val Val Ala Ser Lys Ala Phe Pro Gln Val Thr
130 135 140

Phe His Val Ile Gly Ser Gly Met Gly Arg His Pro Gly Tyr Gly Asp
145 150 155 160

Asn Val Ile Val Tyr Gly Glu Met Lys His Ala Gln Thr Ile Gly Tyr
165 170 175

-continued

```
Ile Lys His Ala Arg Phe Gly Ile Ala Pro Tyr Ala Ser Glu Gln Val
            180                 185                 190

Pro Val Tyr Leu Ala Asp Ser Ser Met Lys Leu Leu Gln Tyr Asp Phe
        195                 200                 205

Phe Gly Leu Pro Ala Val Cys Pro Asn Ala Val Val Gly Pro Tyr Lys
    210                 215                 220

Ser Arg Phe Gly Tyr Thr Pro Gly Asn Ala Asp Ser Val Ile Ala Ala
225                 230                 235                 240

Ile Thr Gln Ala Leu Glu Ala Pro Arg Val Arg Tyr Arg Gln Cys Leu
                245                 250                 255

Asn Trp Ser Asp Thr Thr Asp Arg Val Leu Asp Pro Arg Ala Tyr Pro
            260                 265                 270

Glu Thr Arg Leu Tyr Pro His Pro Pro Thr Ala Ala Pro Gln Leu Ser
        275                 280                 285

Ser Glu Ala Ala Leu Ser His
    290                 295


<210> SEQ ID NO 28
<211> LENGTH: 263
<212> TYPE: PRT
<213> ORGANISM: Xanthomonas compestris

<400> SEQUENCE: 28

Met His Gly Gln Pro Ala Gly Val Glu Thr Ala Thr Val Ser Ala Ala
1               5                   10                  15

Thr Pro Ala Gln Gly Val Val Ile Pro Leu Gly Gly Phe Pro Val Leu
            20                  25                  30

Ser Thr Thr Gln Glu Ala Phe Ala Leu Asp Leu Phe His Ala Leu Ala
        35                  40                  45

Ala His Gln Pro Arg Arg Val Phe Phe Ala Asn Thr Asn Phe Ile Val
    50                  55                  60

Gln Cys Gln Ala Leu Arg Ala Arg Met Gln Ala Pro Ala Val Arg Ile
65                  70                  75                  80

Val Asn Asp Gly Ile Gly Met Asp Leu Ala Ala Arg Leu Ile His Gly
                85                  90                  95

Arg Arg Phe Ala Gly Asn Leu Asn Gly Thr Asp Leu Ile Pro Tyr Leu
            100                 105                 110

Cys Arg Glu Ala Ala Gln Pro Leu Lys Phe Phe Leu Leu Gly Gly Arg
        115                 120                 125

Pro Gly Val Gly Lys Thr Ala Ala Ala Thr Leu Thr Gly Thr Leu Gly
    130                 135                 140

Gln Gln Val Val Gly Met Cys Asp Gly Tyr Gly Glu Phe Ala Ala Ala
145                 150                 155                 160

Gly Glu Gly Leu Ala Glu Arg Ile Asn Arg Ser Gly Ala Asp Val Leu
                165                 170                 175

Leu Val Ala Phe Gly Asn Pro Leu Gln Glu Arg Trp Ile Leu Asp His
            180                 185                 190

Ser Glu Ala Leu Gln Val Pro Leu Val Phe Gly Val Gly Ala Leu Leu
        195                 200                 205

Asp Phe Leu Ser Gly Thr Ala Lys Arg Ala Pro Asn Trp Val Arg Arg
    210                 215                 220

Leu His Met Glu Trp Met Tyr Arg Leu Leu Asn Glu Pro Arg Arg Leu
225                 230                 235                 240
```

-continued

| | | | | | | | | | | | | | | | |
|---|---|---|---|---|---|---|---|---|---|---|---|---|---|---|---|
| Leu | Lys | Arg | Tyr | Ser | Trp | Asp | Leu | Leu | Val | Phe | Phe | Arg | Thr | Cys | Leu |
| | | | | 245 | | | | | 250 | | | | | 255 | |
| Arg | Ala | Gly | Lys | Gln | Leu | Ala | | | | | | | | | |
| | | | 260 | | | | | | | | | | | | |